(12) United States Patent
Nguyen et al.

(10) Patent No.: US 9,005,283 B2
(45) Date of Patent: *Apr. 14, 2015

(54) INTRAOCULAR LENS

(75) Inventors: Tuan Anh Nguyen, Orange, CA (US); Gholam-Reza Zadno-Azizi, Fremont, CA (US); Scott Evans, Santa Ana, CA (US)

(73) Assignee: Visiogen Inc., Santa Ana, CA (US)

( * ) Notice: Subject to any disclaimer, the term of this patent is extended or adjusted under 35 U.S.C. 154(b) by 215 days.

This patent is subject to a terminal disclaimer.

(21) Appl. No.: 13/588,629

(22) Filed: Aug. 17, 2012

(65) Prior Publication Data

US 2012/0310342 A1    Dec. 6, 2012

Related U.S. Application Data

(63) Continuation of application No. 12/861,732, filed on Aug. 23, 2010, now Pat. No. 8,246,679, which is a continuation of application No. 10/958,871, filed on Oct. 5, 2004, now Pat. No. 7,780,729.

(60) Provisional application No. 60/563,238, filed on Apr. 16, 2004.

(51) Int. Cl.
*A61F 2/16* (2006.01)

(52) U.S. Cl.
CPC ............ *A61F 2/1616* (2013.01); *A61F 2/1629* (2013.01); *A61F 2/1648* (2013.01)

(58) Field of Classification Search
CPC .... A61F 2/1616; A61F 2/1629; A61F 2/1648
USPC ........... 623/6.34, 6.37, 6.39, 6.4, 6.46
See application file for complete search history.

(56) References Cited

U.S. PATENT DOCUMENTS

| 1,483,509 A | 2/1924 | Bugbee |
| 2,129,305 A | 9/1938 | Feinbloom |

(Continued)

FOREIGN PATENT DOCUMENTS

| AU | 3225789 | 10/1989 |
| DE | 2702117 | 7/1978 |

(Continued)

OTHER PUBLICATIONS

ASCRS Symposium of Cataracts IOL and Refractive Surgery. ASOA Congress on Ophthalmic Practice Management. Clinical & Surgical Staff Program. Partial Program re: ASCRS Symposium, Showing Video Tape Shown between Apr. 10-14, 1999.

(Continued)

*Primary Examiner* — David H Willse
*Assistant Examiner* — Javier Blanco
(74) *Attorney, Agent, or Firm* — Visiogen Inc.

(57) ABSTRACT

An accommodating intraocular lens has an anterior portion including an anterior viewing element and an anterior biasing element connected to the anterior viewing element. A posterior portion has a posterior viewing element and a posterior biasing element connected to the posterior viewing element. The anterior and posterior biasing elements are connected at first and second apices. First and second distending members are connected to the posterior portion. The first and second distending members extend to locations significantly anterior of an anterior side of the posterior viewing element.

8 Claims, 35 Drawing Sheets

(56) References Cited

U.S. PATENT DOCUMENTS

| | | |
|---|---|---|
| 2,274,142 A | 2/1942 | Houchin |
| 2,405,989 A | 8/1946 | Beach |
| 2,511,517 A | 6/1950 | Spiegel |
| 3,031,927 A | 5/1962 | Wesley |
| 3,034,403 A | 5/1962 | Neefe |
| RE25,286 E | 11/1962 | de Carte |
| 3,210,894 A | 10/1965 | Bentley et al. |
| 3,222,432 A | 12/1965 | Grandperret |
| 3,227,507 A | 1/1966 | Feinbloom |
| 3,339,997 A | 9/1967 | Wesley |
| 3,420,006 A | 1/1969 | Barnett |
| 3,431,327 A | 3/1969 | Tsuetaki |
| 3,482,906 A | 12/1969 | Volk |
| 3,542,461 A | 11/1970 | Girard et al. |
| 3,693,301 A | 9/1972 | Lemaitre |
| 3,760,045 A | 9/1973 | Thiele et al. |
| 3,922,728 A | 12/1975 | Krasnov |
| 3,932,148 A | 1/1976 | Krewalk, Sr. |
| 4,055,378 A | 10/1977 | Feneberg |
| 4,062,629 A | 12/1977 | Winthrop |
| 4,162,122 A | 7/1979 | Cohen |
| 4,195,919 A | 4/1980 | Shelton |
| 4,199,231 A | 4/1980 | Evans |
| 4,210,391 A | 7/1980 | Cohen |
| 4,240,163 A | 12/1980 | Galin |
| 4,240,719 A | 12/1980 | Guilino et al. |
| 4,253,199 A | 3/1981 | Banko |
| 4,254,509 A | 3/1981 | Tennant |
| 4,274,717 A | 6/1981 | Davenport |
| 4,307,945 A | 12/1981 | Kitchen et al. |
| 4,315,673 A | 2/1982 | Guilino et al. |
| 4,316,293 A | 2/1982 | Bayers |
| 4,338,005 A | 7/1982 | Cohen |
| 4,340,283 A | 7/1982 | Cohen |
| 4,370,760 A | 2/1983 | Kelman |
| 4,377,329 A | 3/1983 | Poler |
| 4,402,579 A | 9/1983 | Poler |
| 4,404,694 A | 9/1983 | Kelman |
| 4,409,691 A | 10/1983 | Levy |
| 4,418,991 A | 12/1983 | Breger |
| 4,426,741 A | 1/1984 | Bittner |
| 4,476,591 A | 10/1984 | Arnott |
| 4,504,982 A | 3/1985 | Burk |
| 4,551,864 A | 11/1985 | Akhavi |
| 4,560,383 A | 12/1985 | Leiske |
| 4,573,775 A | 3/1986 | Bayshort |
| 4,580,882 A | 4/1986 | Nuchman et al. |
| 4,596,578 A | 6/1986 | Kelman |
| 4,618,228 A | 10/1986 | Baron et al. |
| 4,618,229 A | 10/1986 | Jacobstein et al. |
| 4,636,049 A | 1/1987 | Blaker |
| 4,636,210 A | 1/1987 | Hoffer |
| 4,636,211 A | 1/1987 | Nielsen et al. |
| 4,637,697 A | 1/1987 | Freeman |
| 4,641,934 A | 2/1987 | Freeman |
| 4,655,770 A | 4/1987 | Gupta et al. |
| 4,666,445 A | 5/1987 | Tillay |
| 4,676,792 A | 6/1987 | Praeger |
| 4,687,484 A | 8/1987 | Kaplan |
| 4,693,572 A | 9/1987 | Tsuetaki et al. |
| RE32,525 E | 10/1987 | Pannu |
| 4,702,244 A | 10/1987 | Mazzocco |
| 4,704,016 A | 11/1987 | de Carle |
| 4,720,286 A | 1/1988 | Bailey et al. |
| 4,725,278 A | 2/1988 | Shearing |
| 4,731,078 A | 3/1988 | Stoy et al. |
| 4,752,123 A | 6/1988 | Blaker |
| 4,759,762 A | 7/1988 | Grendahl |
| 4,769,033 A | 9/1988 | Nordan |
| 4,780,154 A | 10/1988 | Mori et al. |
| 4,790,847 A | 12/1988 | Woods |
| 4,813,955 A | 3/1989 | Achatz et al. |
| 4,830,481 A | 5/1989 | Futhey et al. |
| 4,842,601 A | 6/1989 | Smith |
| 4,881,804 A | 11/1989 | Cohen |
| 4,883,485 A | 11/1989 | Patel |
| 4,888,012 A | 12/1989 | Horn et al. |
| 4,888,015 A | 12/1989 | Domino |
| 4,890,912 A | 1/1990 | Visser |
| 4,890,913 A | 1/1990 | De Carle |
| 4,892,543 A | 1/1990 | Turley |
| 4,898,461 A | 2/1990 | Portney |
| 4,902,293 A | 2/1990 | Feaster |
| 4,906,246 A | 3/1990 | Grendahl |
| 4,917,681 A | 4/1990 | Nordan |
| 4,919,663 A | 4/1990 | Grendahl |
| 4,921,496 A | 5/1990 | Grendahl |
| 4,923,296 A | 5/1990 | Erickson |
| 4,929,289 A | 5/1990 | Moriya et al. |
| 4,932,966 A | 6/1990 | Christie et al. |
| 4,932,968 A | 6/1990 | Caldwell et al. |
| 4,932,971 A | 6/1990 | Kelman |
| 4,938,583 A | 7/1990 | Miller |
| 4,946,469 A | 8/1990 | Sarfarazi |
| 4,955,902 A | 9/1990 | Kelman |
| 4,963,148 A | 10/1990 | Sulc et al. |
| 4,976,534 A | 12/1990 | Miege et al. |
| 4,976,732 A | 12/1990 | Vorosmarthy |
| 4,990,159 A | 2/1991 | Kraff |
| 4,994,082 A | 2/1991 | Richards et al. |
| 4,994,083 A | 2/1991 | Sulc et al. |
| 5,000,559 A | 3/1991 | Takahashi et al. |
| 5,002,382 A | 3/1991 | Seidner |
| 5,019,098 A | 5/1991 | Mercier |
| 5,019,099 A | 5/1991 | Nordan |
| 5,047,052 A | 9/1991 | Dubroff |
| 5,071,432 A | 12/1991 | Baikoff |
| 5,089,024 A | 2/1992 | Christie et al. |
| 5,096,285 A | 3/1992 | Silberman |
| 5,112,351 A | 5/1992 | Christie et al. |
| 5,147,397 A | 9/1992 | Christ et al. |
| 5,152,788 A | 10/1992 | Isaacson et al. |
| 5,152,789 A | 10/1992 | Willis |
| 5,158,572 A | 10/1992 | Nielsen |
| 5,166,711 A | 11/1992 | Portney |
| 5,166,712 A | 11/1992 | Portney |
| 5,171,266 A | 12/1992 | Wiley et al. |
| 5,171,320 A | 12/1992 | Nishi |
| 5,173,723 A | 12/1992 | Volk |
| 5,192,317 A | 3/1993 | Kalb |
| 5,192,318 A | 3/1993 | Schneider |
| 5,201,762 A | 4/1993 | Hauber |
| 5,225,858 A | 7/1993 | Portney |
| 5,258,025 A | 11/1993 | Fedorov et al. |
| 5,260,727 A | 11/1993 | Oksman et al. |
| 5,270,744 A | 12/1993 | Portney |
| 5,275,623 A | 1/1994 | Sarfarazi |
| 5,326,347 A | 7/1994 | Cumming |
| 5,354,335 A | 10/1994 | Lipshitz et al. |
| 5,358,520 A | 10/1994 | Patel |
| 5,391,202 A | 2/1995 | Lipshitz et al. |
| RE34,998 E | 7/1995 | Langerman |
| 5,443,506 A | 8/1995 | Garabet |
| 5,476,514 A | 12/1995 | Cumming |
| 5,480,428 A | 1/1996 | Fedorov et al. |
| 5,489,302 A | 2/1996 | Skottun |
| 5,496,366 A | 3/1996 | Cumming |
| 5,503,165 A | 4/1996 | Schachar |
| 5,521,656 A | 5/1996 | Portney |
| 5,522,891 A | 6/1996 | Klaas |
| 5,549,760 A | 8/1996 | Becker |
| 5,562,731 A | 10/1996 | Cumming |
| 5,578,081 A | 11/1996 | McDonald |
| 5,607,472 A | 3/1997 | Thompson |
| 5,620,720 A | 4/1997 | Glick et al. |
| 5,628,795 A | 5/1997 | Langerman |
| 5,628,796 A | 5/1997 | Suzuki |
| 5,652,014 A | 7/1997 | Galin et al. |
| 5,652,638 A | 7/1997 | Roffman et al. |
| 5,653,754 A | 8/1997 | Nakajima et al. |
| 5,657,108 A | 8/1997 | Portney |
| 5,674,282 A | 10/1997 | Cumming |
| 5,682,223 A | 10/1997 | Menezes et al. |
| 5,684,560 A | 11/1997 | Roffman et al. |

(56) References Cited

U.S. PATENT DOCUMENTS

| | | | |
|---|---|---|---|
| 5,725,576 A | 3/1998 | Fedorov et al. | |
| 5,766,244 A | 6/1998 | Binder | |
| 5,769,890 A | 6/1998 | McDonald | |
| 5,776,191 A | 7/1998 | Mazzocco | |
| 5,776,192 A | 7/1998 | McDonald | |
| 5,800,533 A | 9/1998 | Eggleston et al. | |
| 5,814,103 A | 9/1998 | Lipshitz et al. | |
| 5,824,074 A | 10/1998 | Koch | |
| 5,843,188 A | 12/1998 | McDonald | |
| 5,876,442 A | 3/1999 | Lipshitz et al. | |
| 5,928,283 A | 7/1999 | Gross et al. | |
| 5,968,094 A | 10/1999 | Werblin et al. | |
| 5,984,962 A | 11/1999 | Anello et al. | |
| 6,013,101 A | 1/2000 | Israel | |
| 6,096,078 A | 8/2000 | McDonald | |
| 6,106,554 A | 8/2000 | Bretton | |
| 6,113,633 A | 9/2000 | Portney | |
| 6,117,171 A | 9/2000 | Skottun | |
| 6,120,538 A | 9/2000 | Rizzo et al. | |
| 6,136,026 A | 10/2000 | Israel | |
| 6,176,878 B1 | 1/2001 | Gwon et al. | |
| 6,197,058 B1 | 3/2001 | Portney | |
| 6,197,059 B1 | 3/2001 | Cumming | |
| 6,200,342 B1 | 3/2001 | Tassignon | |
| 6,217,612 B1 | 4/2001 | Woods | |
| 6,231,603 B1 | 5/2001 | Lang et al. | |
| 6,238,433 B1 | 5/2001 | Portney | |
| 6,258,123 B1 | 7/2001 | Young et al. | |
| 6,277,146 B1 | 8/2001 | Peyman et al. | |
| 6,280,471 B1 | 8/2001 | Peyman et al. | |
| RE37,387 E | 9/2001 | Brady et al. | |
| 6,299,641 B1 | 10/2001 | Woods | |
| 6,327,772 B1 | 12/2001 | Zadno-Azizi et al. | |
| 6,342,073 B1 | 1/2002 | Cumming et al. | |
| 6,358,280 B1 | 3/2002 | Herrick | |
| 6,387,126 B1 | 5/2002 | Cumming | |
| 6,406,494 B1 | 6/2002 | Laguette et al. | |
| 6,423,094 B1 | 7/2002 | Sarfarazi | |
| 6,443,985 B1 | 9/2002 | Woods | |
| 6,450,642 B1 | 9/2002 | Jethmalani et al. | |
| 6,454,802 B1 | 9/2002 | Bretton et al. | |
| 6,464,725 B2 | 10/2002 | Skottun | |
| 6,478,821 B1 | 11/2002 | Laguette et al. | |
| 6,488,708 B2 | 12/2002 | Sarfarazi | |
| 6,494,911 B2 | 12/2002 | Cumming | |
| 6,503,275 B1 | 1/2003 | Cumming | |
| 6,503,276 B2 | 1/2003 | Lang et al. | |
| 6,524,340 B2 | 2/2003 | Israel | |
| 6,524,350 B2 | 2/2003 | Buentello et al. | |
| 6,533,813 B1 | 3/2003 | Lin et al. | |
| 6,547,822 B1 | 4/2003 | Lang | |
| 6,551,354 B1 | 4/2003 | Ghazizadeh et al. | |
| 6,554,859 B1 | 4/2003 | Lang et al. | |
| 6,558,420 B2 | 5/2003 | Green | |
| 6,599,317 B1 | 7/2003 | Weinschenk, III et al. | |
| 6,616,691 B1 | 9/2003 | Tran | |
| 6,616,692 B1 | 9/2003 | Glick et al. | |
| 6,645,246 B1 | 11/2003 | Weinschenk et al. | |
| 6,660,035 B1 | 12/2003 | Lang et al. | |
| 6,761,737 B2 | 7/2004 | Zadno-Azizi et al. | |
| 6,764,511 B2 | 7/2004 | Zadno-Azizi et al. | |
| 6,767,363 B1 | 7/2004 | Bandhauer et al. | |
| 6,786,934 B2 | 9/2004 | Zadno-Azizi et al. | |
| 6,818,017 B1 | 11/2004 | Shu | |
| 6,818,158 B2 | 11/2004 | Pham et al. | |
| 6,846,326 B2 | 1/2005 | Zadno-Azizi et al. | |
| 6,858,040 B2 | 2/2005 | Nguyen et al. | |
| 6,884,261 B2 | 4/2005 | Zadno-Azizi et al. | |
| 6,884,263 B2 | 4/2005 | Valyunin et al. | |
| 6,899,732 B2 | 5/2005 | Zadno-Azizi et al. | |
| 6,926,736 B2 | 8/2005 | Peng et al. | |
| 7,041,134 B2 | 5/2006 | Nguyen et al. | |
| 7,087,080 B2 | 8/2006 | Zadno-Azizi et al. | |
| 7,097,660 B2 | 8/2006 | Portney | |
| 7,118,596 B2 | 10/2006 | Zadno-Azizi et al. | |
| 7,118,597 B2 | 10/2006 | Miller et al. | |
| 7,125,422 B2 | 10/2006 | Woods et al. | |
| 7,198,640 B2 | 4/2007 | Nguyen | |
| 7,226,478 B2 | 6/2007 | Ting et al. | |
| 7,238,201 B2 | 7/2007 | Portney et al. | |
| 7,452,362 B2 | 11/2008 | Zadno-Azizi et al. | |
| 7,452,378 B2 | 11/2008 | Zadno-Azizi et al. | |
| 7,662,180 B2 | 2/2010 | Paul et al. | |
| 7,744,603 B2 | 6/2010 | Zadno-Azizi et al. | |
| 7,744,646 B2 | 6/2010 | Zadno-Azizi et al. | |
| 7,780,729 B2 | 8/2010 | Nguyen et al. | |
| 2001/0001836 A1 | 5/2001 | Cumming | |
| 2002/0002404 A1 | 1/2002 | Sarfarazi | |
| 2002/0004682 A1 | 1/2002 | Zhou et al. | |
| 2002/0045937 A1 | 4/2002 | Sarfarazi | |
| 2002/0068971 A1 | 6/2002 | Cumming | |
| 2002/0072795 A1 | 6/2002 | Green | |
| 2002/0095212 A1 | 7/2002 | Boehm | |
| 2002/0120329 A1 | 8/2002 | Lang et al. | |
| 2002/0138140 A1 | 9/2002 | Hanna | |
| 2002/0193876 A1 | 12/2002 | Lang et al. | |
| 2003/0002404 A1 | 1/2003 | Maekawa | |
| 2003/0018384 A1 | 1/2003 | Valyunin et al. | |
| 2003/0033013 A1 | 2/2003 | Callahan et al. | |
| 2003/0050695 A1 | 3/2003 | Lin et al. | |
| 2003/0050696 A1 | 3/2003 | Cumming | |
| 2003/0050697 A1 | 3/2003 | Paul | |
| 2003/0060878 A1 | 3/2003 | Shadduck | |
| 2003/0060881 A1 | 3/2003 | Glick et al. | |
| 2003/0078657 A1 | 4/2003 | Zadno-Azizi et al. | |
| 2003/0078658 A1 | 4/2003 | Zadno-Azizi | |
| 2003/0083744 A1 | 5/2003 | Khoury | |
| 2003/0093149 A1 | 5/2003 | Glazier | |
| 2003/0105522 A1 | 6/2003 | Glazier | |
| 2003/0114927 A1 | 6/2003 | Nagamoto | |
| 2003/0130732 A1 | 7/2003 | Sarfarazi | |
| 2003/0187504 A1 | 10/2003 | Weinschenk, III et al. | |
| 2003/0204255 A1 | 10/2003 | Peng et al. | |
| 2004/0015236 A1 | 1/2004 | Sarfarazi | |
| 2004/0082995 A1* | 4/2004 | Woods | 623/6.34 |
| 2004/0158322 A1 | 8/2004 | Shen | |
| 2005/0131535 A1 | 6/2005 | Woods | |
| 2005/0267575 A1 | 12/2005 | Nguyen et al. | |
| 2006/0178741 A1 | 8/2006 | Zadno-Azizi et al. | |
| 2006/0184244 A1 | 8/2006 | Nguyen et al. | |
| 2006/0238702 A1 | 10/2006 | Glick et al. | |
| 2006/0259139 A1 | 11/2006 | Zadno-Azizi et al. | |
| 2006/0271187 A1 | 11/2006 | Zadno-Azizi et al. | |
| 2007/0050025 A1 | 3/2007 | Nguyen et al. | |
| 2007/0078515 A1 | 4/2007 | Brady | |
| 2007/0106377 A1 | 5/2007 | Smith et al. | |
| 2007/0108643 A1 | 5/2007 | Zadno-Azizi et al. | |

FOREIGN PATENT DOCUMENTS

| | | |
|---|---|---|
| DE | 3246306 | 6/1984 |
| DE | 19501444 | 7/1996 |
| DE | 10125829 | 11/2002 |
| EP | 0162573 | 11/1985 |
| EP | 0212616 | 3/1987 |
| EP | 246216 | 11/1987 |
| EP | 0329981 | 8/1989 |
| EP | 0337390 A2 | 10/1989 |
| EP | 0337390 A3 | 10/1989 |
| EP | 0342895 | 11/1989 |
| EP | 0351471 | 1/1990 |
| EP | 0420549 | 4/1991 |
| EP | 0336877 | 10/1993 |
| EP | 0566170 | 10/1993 |
| EP | 0691109 | 1/1996 |
| EP | 0897702 | 2/1999 |
| GB | 2058391 | 4/1981 |
| GB | 2124500 | 2/1984 |
| GB | 2129155 | 5/1984 |
| GB | 2146791 | 4/1985 |
| GB | 2192291 | 1/1988 |
| GB | 2215076 | 9/1989 |
| JP | 02-126847 | 5/1990 |
| RU | 2014038 | 6/1994 |

(56) References Cited

FOREIGN PATENT DOCUMENTS

| | | |
|---|---|---|
| RU | 2014039 | 6/1994 |
| WO | WO 84/04449 | 11/1984 |
| WO | WO 85/04566 | 10/1985 |
| WO | WO 86/03961 | 7/1986 |
| WO | WO 87/00299 | 1/1987 |
| WO | WO 87/07496 | 12/1987 |
| WO | WO 89/02251 | 3/1989 |
| WO | WO 89/11672 | 11/1989 |
| WO | WO 94/16648 | 8/1994 |
| WO | WO 95/03783 | 2/1995 |
| WO | WO 96/15734 | 5/1996 |
| WO | WO 96/25126 | 8/1996 |
| WO | WO 97/43984 | 11/1997 |
| WO | WO 99/03427 | 1/1999 |
| WO | WO 99/20206 | 4/1999 |
| WO | WO 00/21467 | 4/2000 |
| WO | WO 00/27315 | 5/2000 |
| WO | WO 00/61036 | 10/2000 |
| WO | WO 00/66037 | 11/2000 |
| WO | WO 01/19289 | 3/2001 |
| WO | WO 01/34067 | 5/2001 |
| WO | WO 01/64136 | 9/2001 |
| WO | WO 01/66042 | 9/2001 |
| WO | WO 02/071983 | 9/2002 |
| WO | WO 03/009051 | 1/2003 |
| WO | WO 03/015657 | 2/2003 |
| WO | WO 03/057081 | 7/2003 |
| WO | WO 03/059196 | 7/2003 |
| WO | WO 03/084441 | 10/2003 |
| WO | WO 03/092552 | 11/2003 |
| WO | WO 2004/000171 | 12/2003 |
| WO | WO 2004/010905 | 2/2004 |
| WO | WO 2004/073559 | 9/2004 |
| WO | WO 2004/090611 | 10/2004 |

OTHER PUBLICATIONS

Tsutomu Hara et al., "Accommodative Intraocular Lens with Spring Action Part 1. Design and Placement in an Excised Animal Eye," Ophthalmic Surgery, Feb. 1990, vol. 21, No. 2, pp. 128-133.

International Search Report for PCT/US2005/012032, Jan. 2004.
Adler-Grinberg, Deborah, "Questioning Our Classical Understanding of Accommodation and Presbyopia," *American Journal of Optometry & Physiological Optics* 1986; 63: 571-580.
Prosecution History of Patent No. 6,764,511, issued Jul. 20, 2004, including Office Actions of Jul. 14, 2003; and Amendments of Nov. 1, 2002, Mar. 14, 2003, Dec. 12, 2003, and Jan. 8, 2004; and Notice of Allowance of Apr. 7, 2004.
Prosecution History of Patent No. 7,452,378, issued Nov. 18, 2008, including Office Actions of Sep. 5, 2007, and Apr. 18, 2008; and Amendments of Jan. 7, 2008, Jun. 17, 2008, Jul. 14, 2008; and Notice of Allowance of Jul. 14, 2008.
Thornton. Accommodation in Pseudophakia, 25. pp. 159-162. Dec. 1992.
"AMO Specs Model AC-21B", AMO Classic Series. PMM IntraOcular Lenses. 1992. 5 pages.
Fechner, et al. "Iris-claw lens in Phakic eyes to correct hyperopia: Preliminary Study". Journal Cataract Refract Surgery, vol. 24, Jan. 1998, pp. 48-56.
Menezo, et al. "Endothelial study of iris-claw phakic lens: Four year follow-up". Journal Cataract Refract Surgery, vol. 24, Aug. 1998, pp. 1039-1049.
Alcon Surgical, Aleon Laboratories. No date given.
Chauvin-Opsia, Azunte ACL (0459) No date given.
Chiron, Clemente Optifit Model SPSP525 Brochure Translation, Dec. 1998.
Chiron Vision, Nunta Mar. 20, 1997. 5 pages.
Hanita Lenses. Ocular Surgery News Intl No date given.
Iolab Corp. Opthalmology Times. Mar. 15, 1995.
Mediphacos Ltd. Ocular Surgery News Intl No date given.
New Elliptical Accommodating IOL for Cataract Surgery shown at ASCRS Symposium on Apr. 1, 1999 (Digital Video Disc).
Opthamed, Inc. OMAC-260. No date given.
Storz. Opthalmics Inc. Model LIZZUV ACL No date given.
Universe IOL Center. Ocular Surgery News Intl No date given.
World Optics, Inc. Ophthalmology Times. Mar. 15, 1995.
U.S. Appl. No. 09/656,661, filed Sep. 7, 2000.
U.S. Appl. No. 09/721,072, filed Nov. 22, 2000.
U.S. Appl. No. 11/426,888, filed on Jun. 27, 2006.

\* cited by examiner

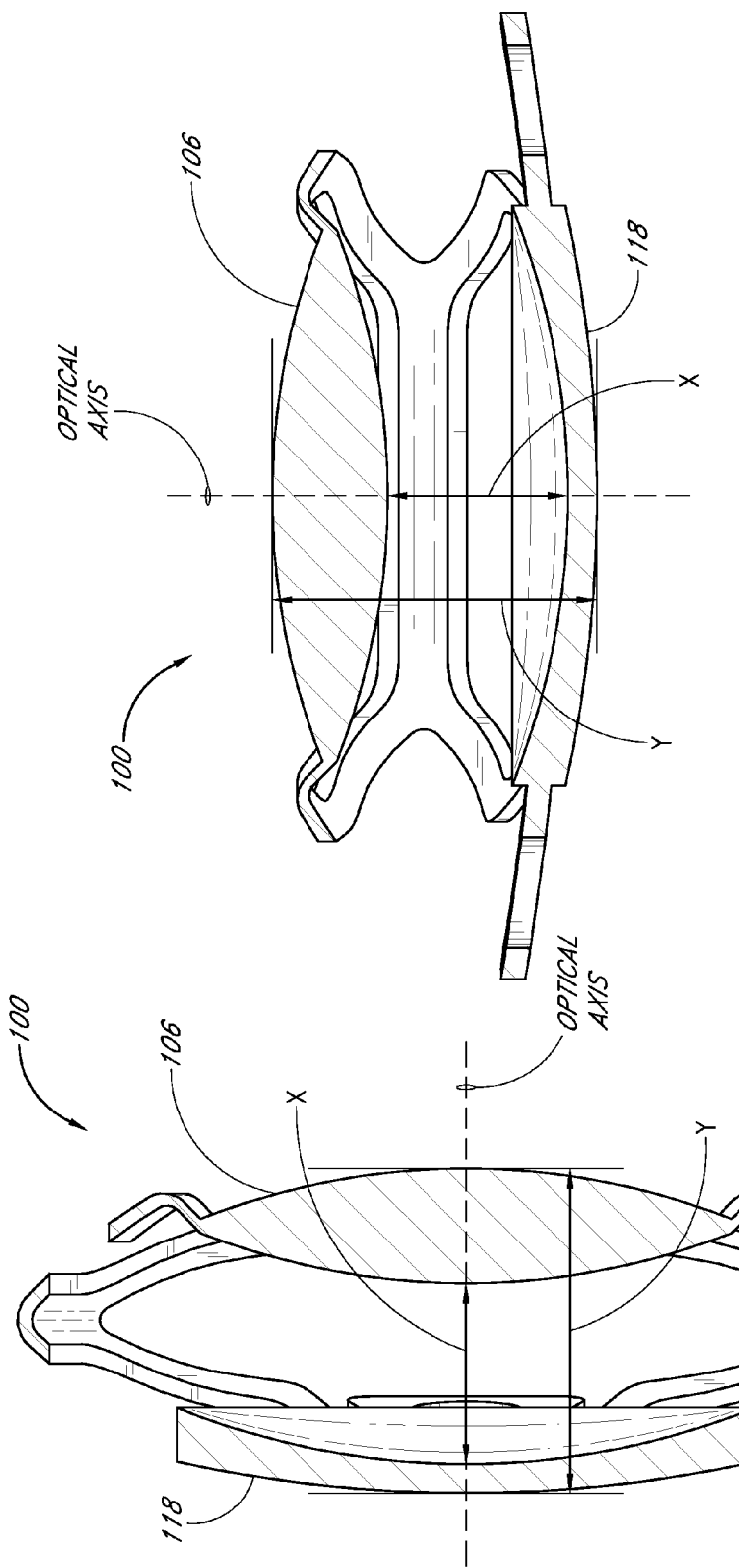

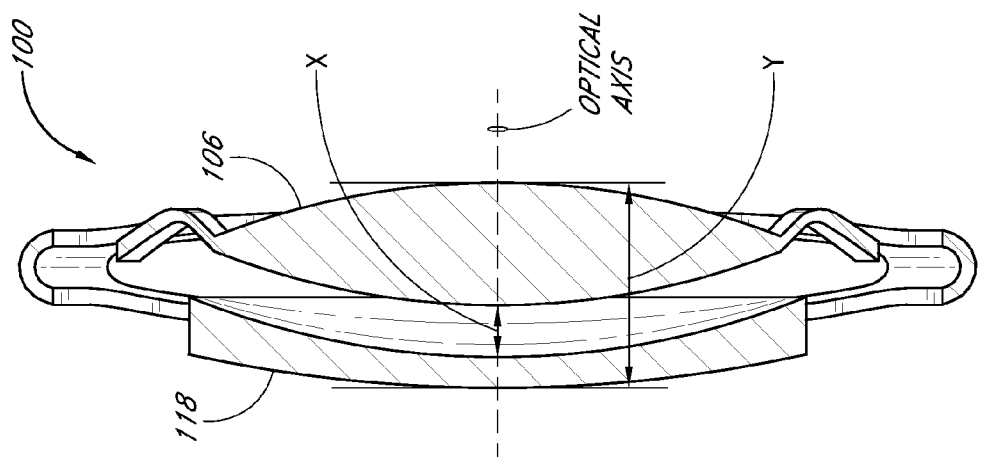
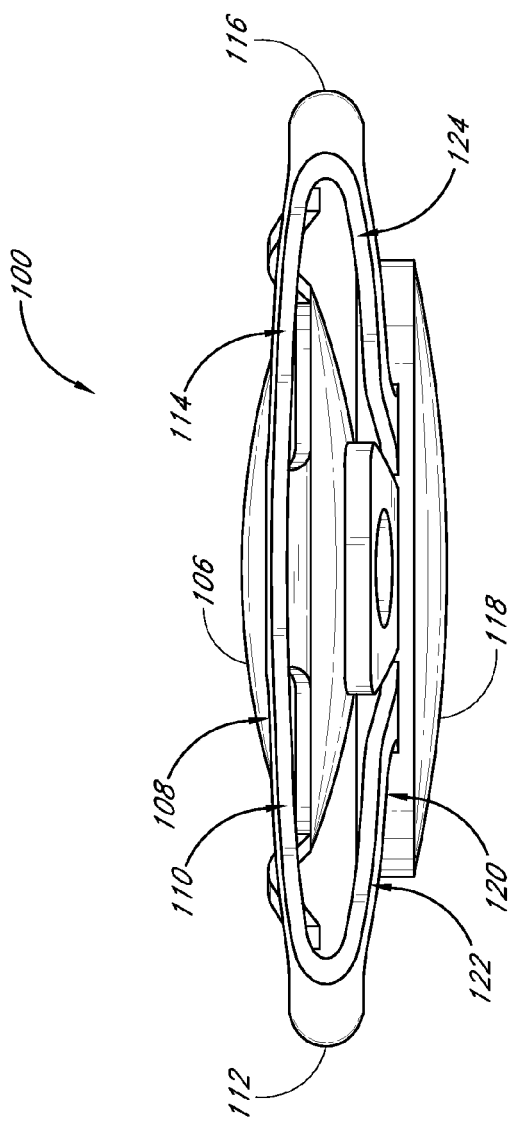

INTRAOCULAR LENS

PRIORITY INFORMATION

This application is a continuation of U.S. patent application Ser. No. 12/861,732, filed on Aug. 23, 2010, which is a continuation of U.S. patent application Ser. No. 10/958,871, filed on Oct. 5, 2004, now U.S. Pat. No. 7,780,729, which claims the benefit of U.S. Provisional Patent Application No. 60/563,238, filed on Apr. 16, 2004. The entire contents of each of the above-identified applications are hereby expressly incorporated by reference herein.

BACKGROUND OF THE INVENTION

1. Field of the Invention

Certain disclosed embodiments relate to intraocular lenses and, more particularly, to intraocular lenses that alter their refractive power in response to action of the ciliary muscle of the eye.

2. Description of the Related Art

The vast majority of cataract operations involve the implantation of an artificial lens following cataract removal. Typically these lenses have a fixed focal length or, in the case of bifocal or multifocal lenses, have several different fixed focal lengths. Such fixed focal-length lenses lack the ability of the natural lens to dynamically change the refractive power of the eye. Certain embodiments of the intraocular lens disclosed herein provide an accommodating lens system which alters its refractive power in response to action of the ciliary muscle, thereby allowing the lens system to bring into focus on the retina images of objects that are both near and far from the eye.

SUMMARY OF THE INVENTION

One aspect of the invention is an accommodating intraocular lens. An anterior portion has an anterior viewing element and an anterior biasing element connected to the anterior viewing element. A posterior portion has a posterior viewing element and a posterior biasing element connected to the posterior viewing element. The anterior and posterior biasing elements are connected at first and second apices. First and second distending members are connected to the posterior portion. Each of the distending members extends to a location significantly anterior of an anterior side of the posterior viewing element. The anterior and posterior portions are connected only at said first and second apices.

Another aspect of the invention is an accommodating intraocular lens. An anterior portion has an anterior viewing element and an anterior biasing element connected to the anterior viewing element. A posterior portion has a posterior viewing element and a posterior biasing element connected to the posterior viewing element. The anterior and posterior biasing elements are connected at first and second apices. First and second distending members are connected to the posterior portion. First and second distending members extend to first and second anterior locations, respectively. Each of the first and second anterior locations is significantly anterior of an anterior side of the posterior viewing element. Each of the first and second anterior locations is spaced from all of the apices.

All of these aspects are intended to be within the scope of the invention herein disclosed. These and other aspects of the invention will become readily apparent to those skilled in the art from the following detailed description of preferred embodiments having reference to the attached figures, the invention not being limited to any particular preferred embodiment(s) disclosed.

BRIEF DESCRIPTION OF THE DRAWINGS

Having thus summarized the general nature of the invention, certain preferred embodiments and modifications thereof will become apparent to those skilled in the art from the detailed description herein having reference to the figures that follow, of which:

FIG. 9 is a side sectional view of the lens system.

FIG. 10 is a top sectional view of the lens system.

FIG. 13 is a side view of the lens system in the unaccommodated state.

FIG. 14 is a side sectional view of the lens system in the unaccommodated state.

DETAILED DESCRIPTION OF PREFERRED EMBODIMENTS

I. The Human Eye and Accommodation

Figure 1:
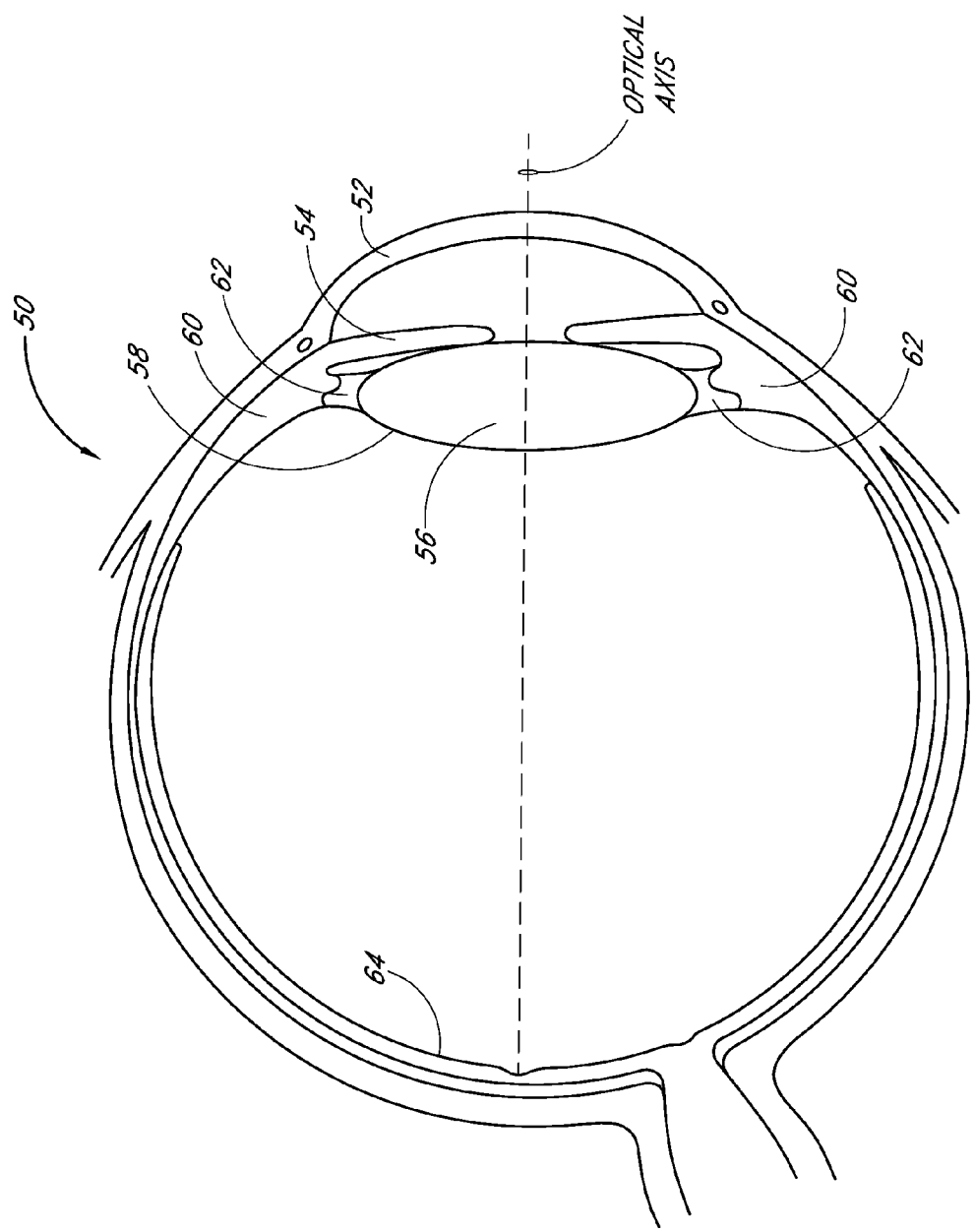
FIG. 1 is a sectional view of the human eye, with the lens in the unaccommodated state.
Figure 2:
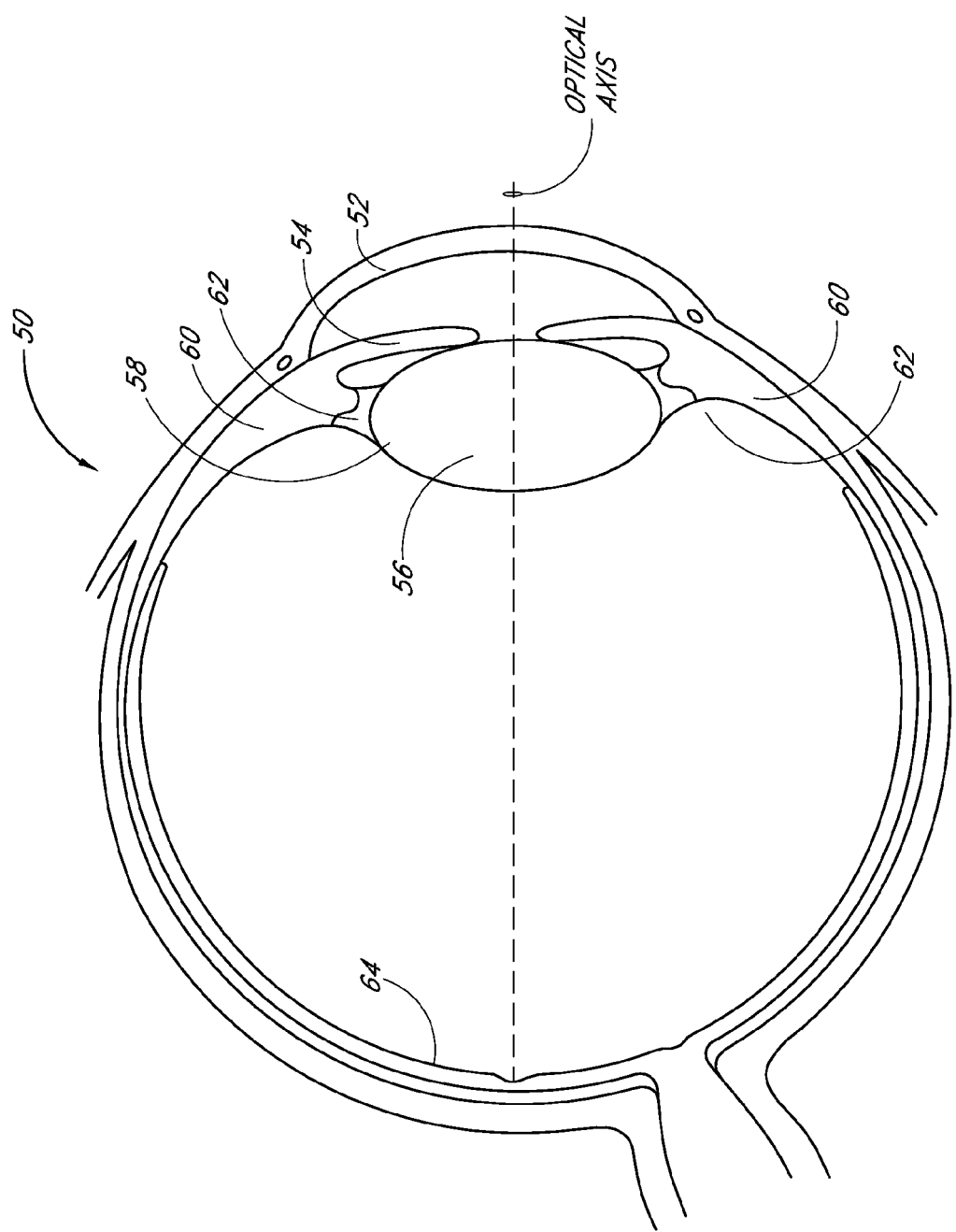
FIG. 2 is a sectional view of the human eye, with the lens in the accommodated state.

FIGS. 1 and 2 show the human eye 50 in section. Of particular relevance to the present disclosure are the cornea 52, the iris 54 and the lens 56, which is situated within the elastic, membranous capsular bag or lens capsule 58. The capsular bag 58 is surrounded by and suspended within the ciliary muscle 60 by ligament-like structures called zonules 62.

As light enters the eye 50, the cornea 52 and the lens 56 cooperate to focus the incoming light and form an image on the retina 64 at the rear of the eye, thus facilitating vision. In the process known as accommodation, the shape of the lens 56 is altered (and its refractive properties thereby adjusted) to allow the eye 50 to focus on objects at varying distances. A typical healthy eye has sufficient accommodation to enable focused vision of objects ranging in distance from infinity (generally defined as over 20 feet from the eye) to very near (closer than 10 inches).

The lens 56 has a natural elasticity, and in its relaxed state assumes a shape that in cross-section resembles a football. Accommodation occurs when the ciliary muscle 60 moves the lens from its relaxed or "unaccommodated" state (shown in FIG. 1) to a contracted or "accommodated" state (shown in FIG. 2). Movement of the ciliary muscle 60 to the relaxed/unaccommodated state increases tension in the zonules 62 and capsular bag 58, which in turn causes the lens 56 to take on a thinner (as measured along the optical axis) or taller shape as shown in FIG. 1. In contrast, when the ciliary muscle 60 is in the contracted/accommodated state, tension in the zonules 62 and capsular bag 58 is decreased and the lens 56 takes on the fatter or shorter shape shown in FIG. 2. When the ciliary muscles 60 contract and the capsular bag 58 and zonules 62 slacken, some degree of tension is maintained in the capsular bag 58 and zonules 62.

II. The Lens System

Structure

Figure 3:
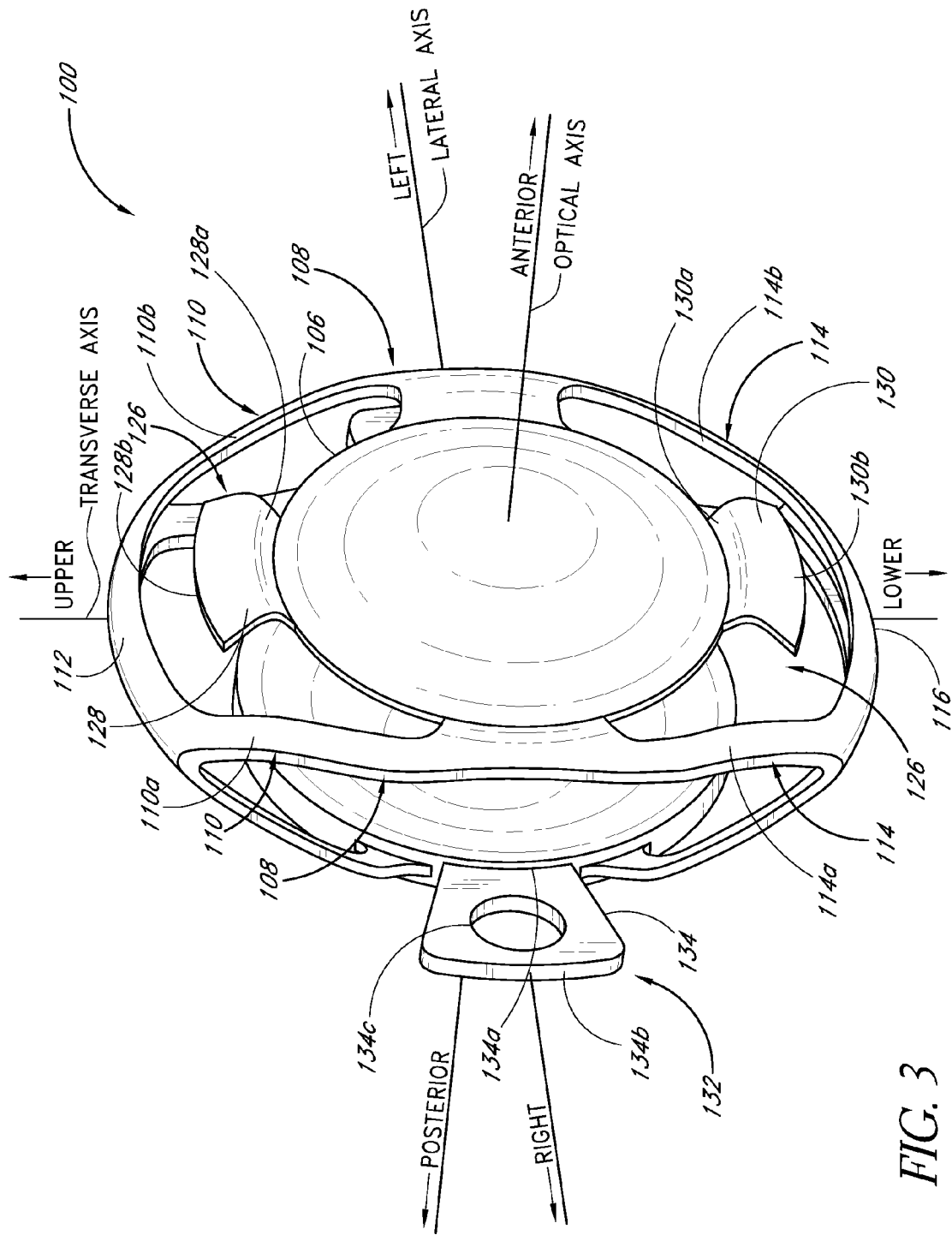
FIG. 3 is a perspective view of one embodiment of an intraocular lens system.

FIGS. 3-17 depict one embodiment of an intraocular lens system 100 which is configured for implantation into the capsular bag 58 in place of the natural lens 56, and is further configured to change the refractive properties of the eye in response to the eye's natural process of accommodation. With reference to FIG. 3, a set of axes is included to illustrate the sense of directional terminology which will be used herein to describe various features of the lens system 100. The terms "anterior" and "posterior" refer to the depicted directions on the optical axis of the lens 100 shown in FIG. 3. When the lens 100 is implanted in an eye, the anterior direction extends toward the cornea and the posterior direction extends toward the retina, with the optical axis of the lens substantially coincident with the optical axis of the eye shown in FIGS. 1 and 2. The terms "left" and "right" refer to the directions shown on the lateral axis, which is orthogonal to the optical axis. In addition, the terms "upper" and "lower" refer to the directions depicted on the transverse axis which is orthogonal to both of the optical axis and the lateral axis.

This system of axes is depicted purely to facilitate description herein; thus, it is not intended to limit the possible orientations which the lens system 100 may assume during use. For example, the lens system 100 may rotate about, or may be displaced along, the optical axis during use without detracting from the performance of the lens. It is clear that, should the lens system 100 be so rotated about the optical axis, the transverse axis may no longer have an upper-lower orientation and the lateral axis may no longer have a left-right orientation, but the lens system 100 will continue to function as it would when oriented as depicted in FIG. 3. Accordingly, when the terms "upper," "lower," "left" or "right" are used in describing features of the lens system 100, such use should not be understood to require the described feature to occupy the indicated position at any or all times during use of the lens system 100. Similarly, such use should not be understood to require the lens system 100 to maintain the indicated orientation at any or all times during use.

Figure 4:
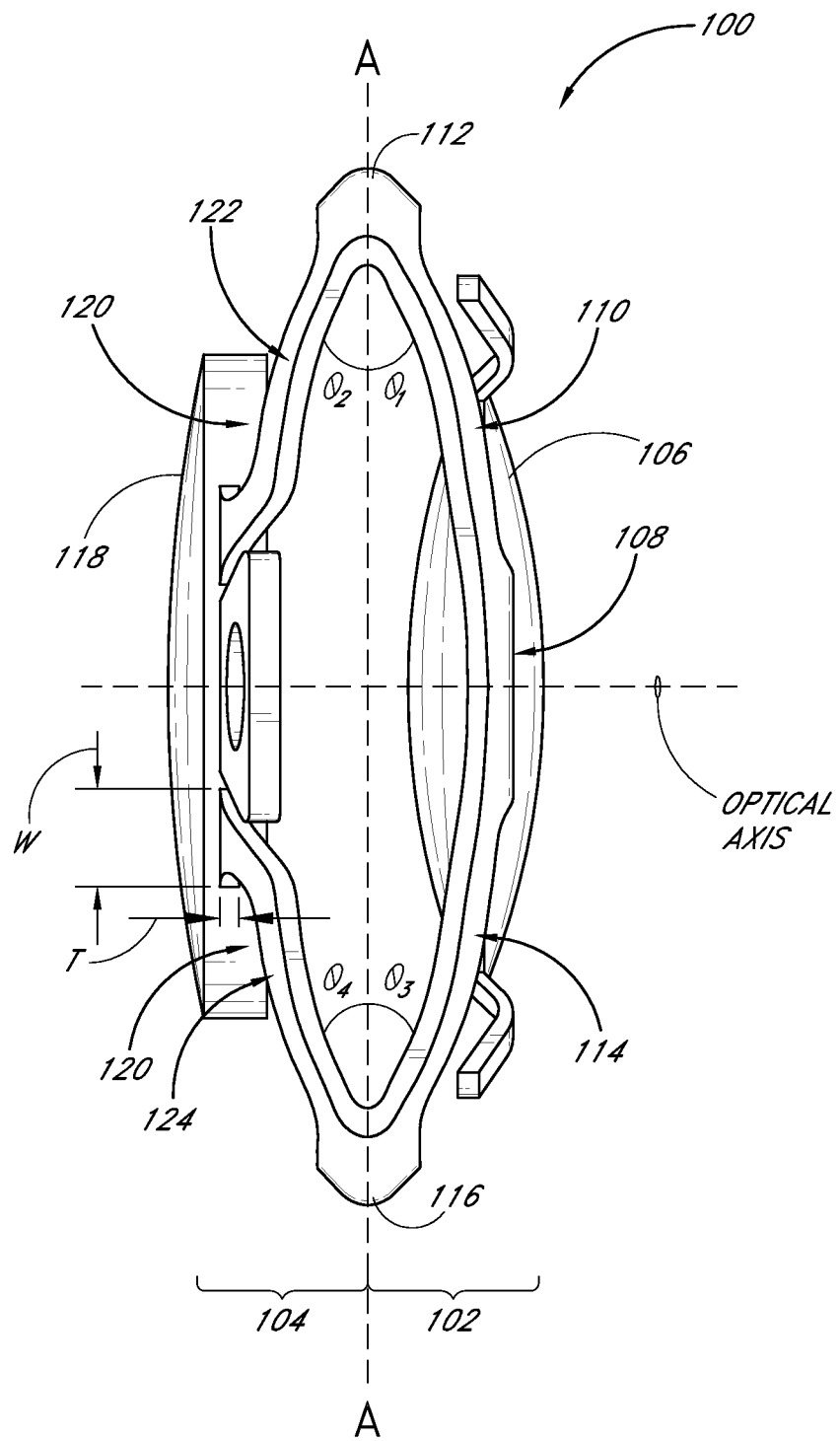
FIG. 4 is a side view of the lens system.

As best seen in FIG. 4, the lens system 100 has an anterior portion 102 which is anterior or forward of the line A-A (which represents a plane substantially orthogonal to the optical axis and intersecting first and second apices 112, 116) and a posterior portion 104 which is posterior or rearward of the line A-A. The anterior portion 102 comprises an anterior viewing element 106 and an anterior biasing element 108. The anterior biasing element 108 in turn comprises a first anterior translation member 110 which extends from the anterior viewing element 106 to the first apex 112 and a second anterior translation member 114 which extends from the anterior viewing element 106 to the second apex 116. In the illustrated embodiment the first anterior translation member 110 comprises a right arm 110a and a left arm 110b (see FIG. 3). In addition, the depicted second anterior translation member 114 comprises a right arm 114a and a left arm 114b. However, in other embodiments either or both of the first and second anterior translation members 110, 114 may comprise a single arm or member, or more than two arms or members.

Figure 5:
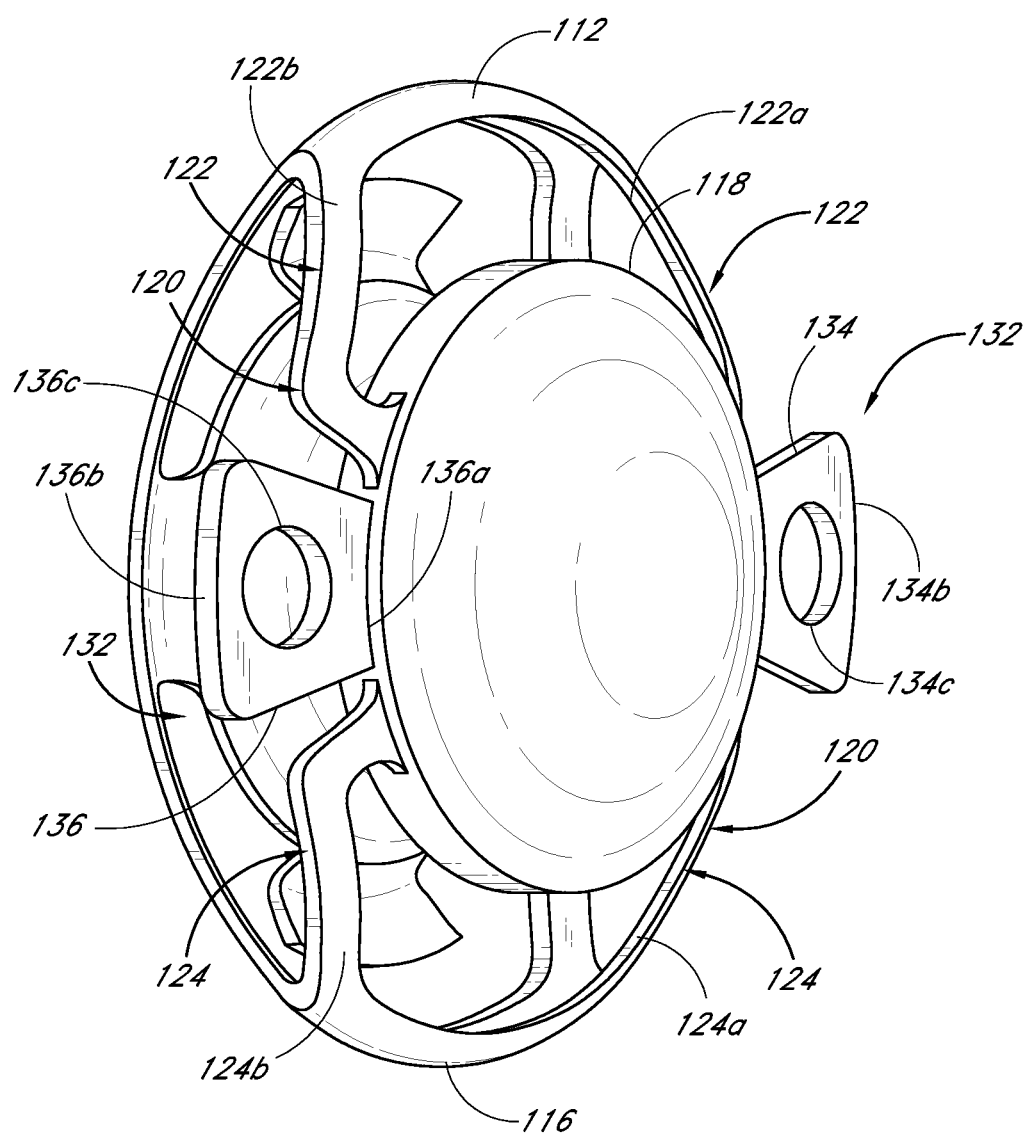
FIG. 5 is a rear perspective view of the lens system.
Figure 7:
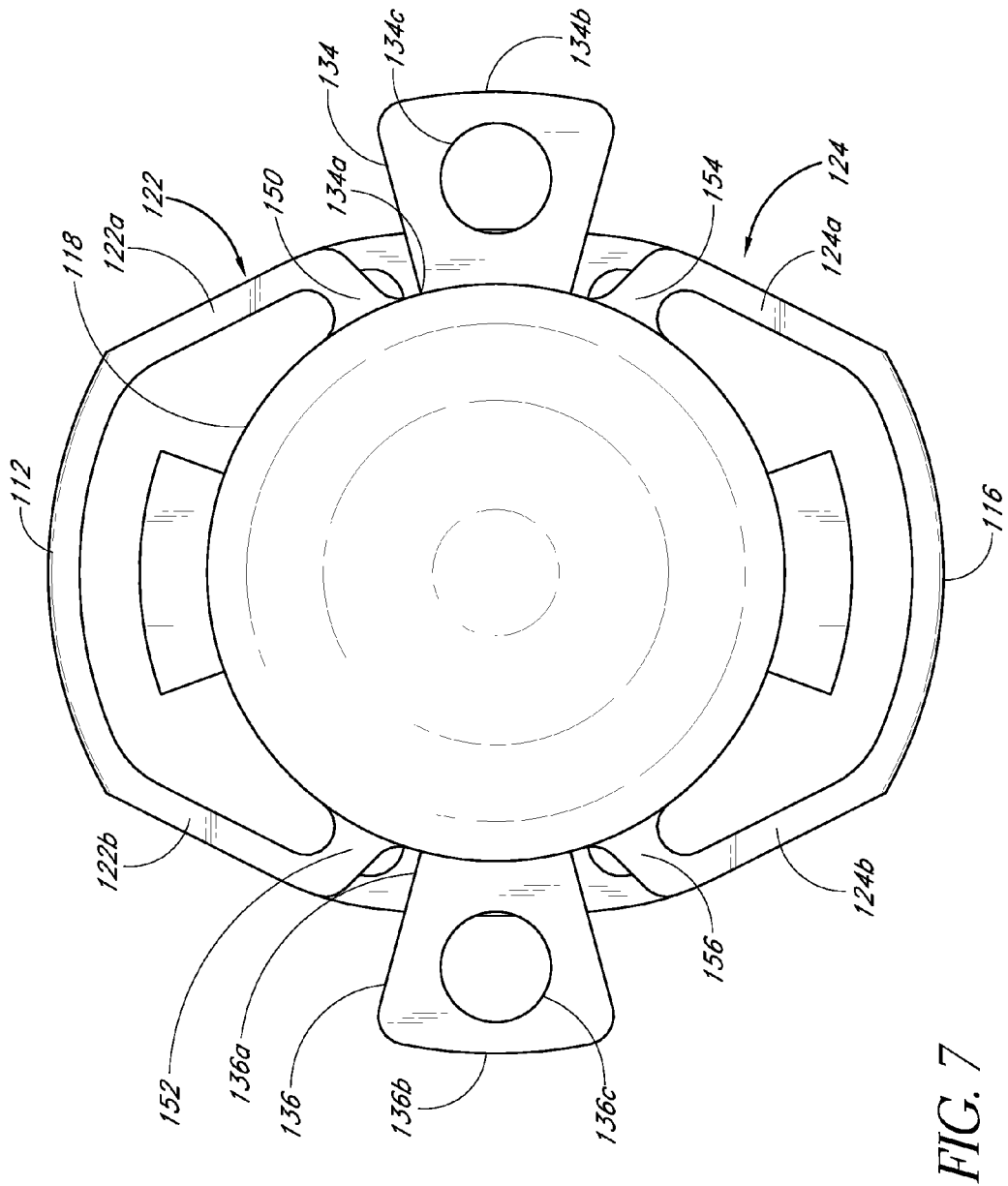
FIG. 7 is a rear view of the lens system.
Figure 8:
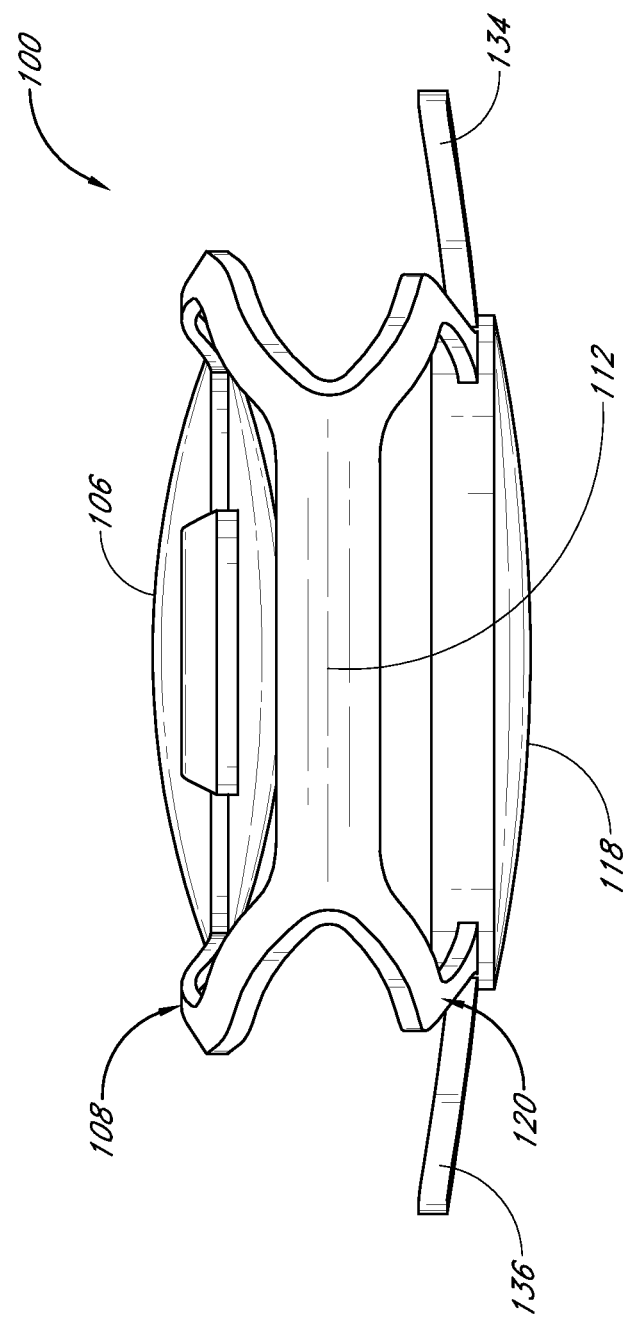
FIG. 8 is a top view of the lens system.
Figure 11:
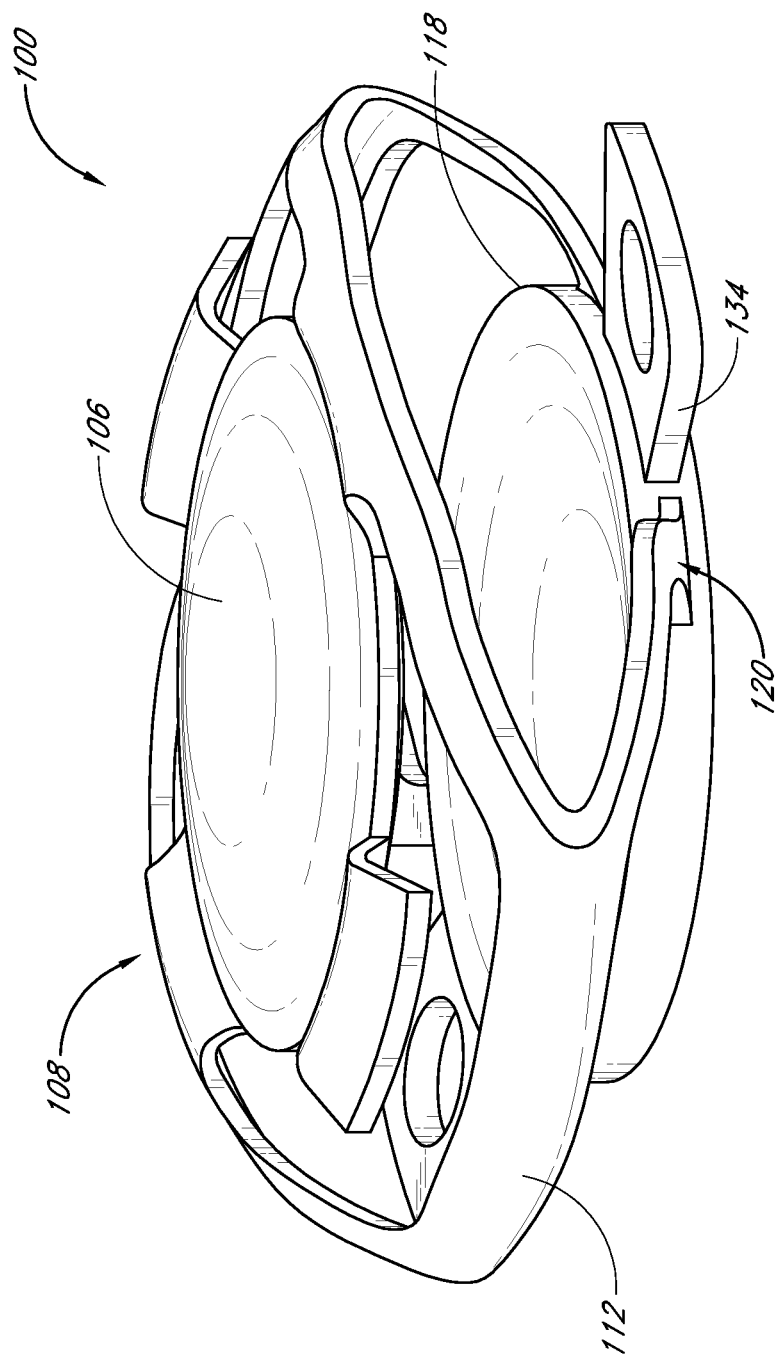
FIG. 11 is a second perspective view of the lens system.
Figure 12:
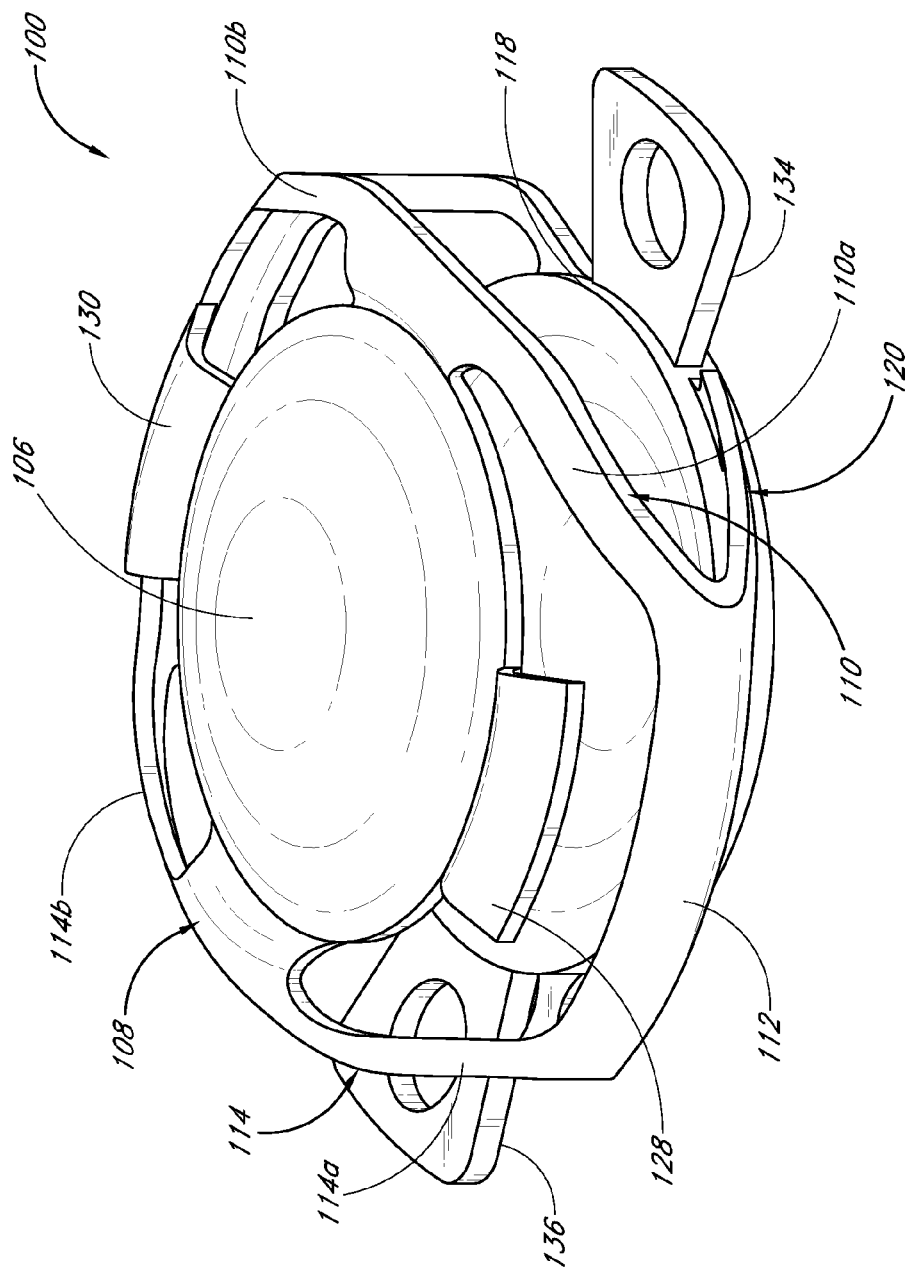
FIG. 12 is a third perspective view of the lens system.
Figure 15:
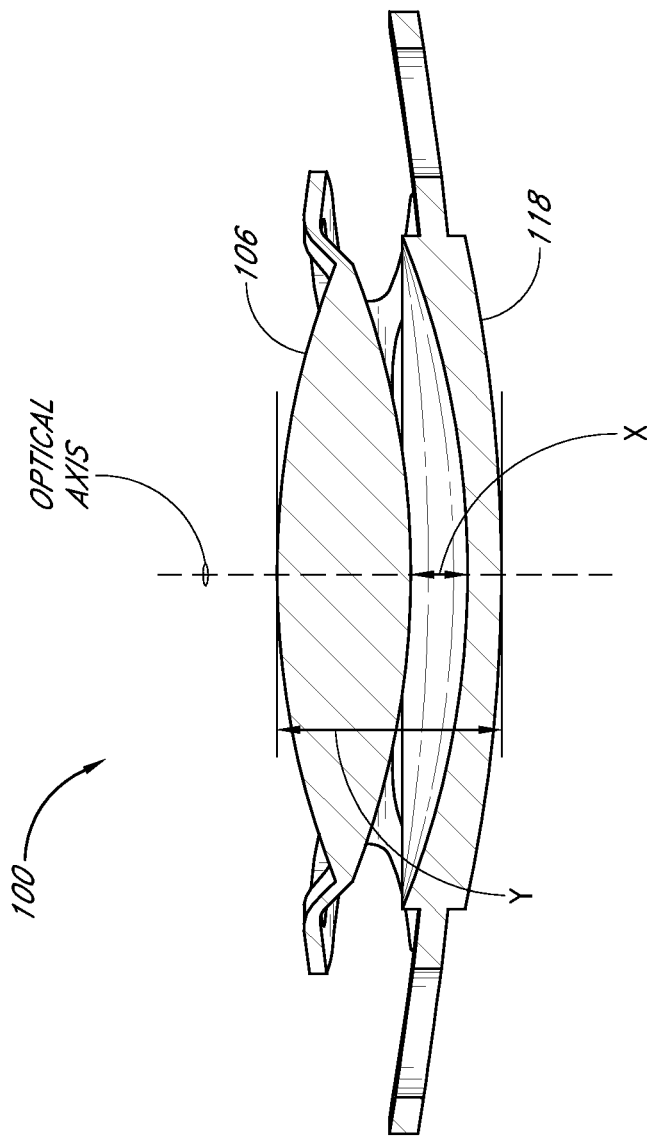
FIG. 15 is a top sectional view of the lens system in the unaccommodated state.
Figure 16:
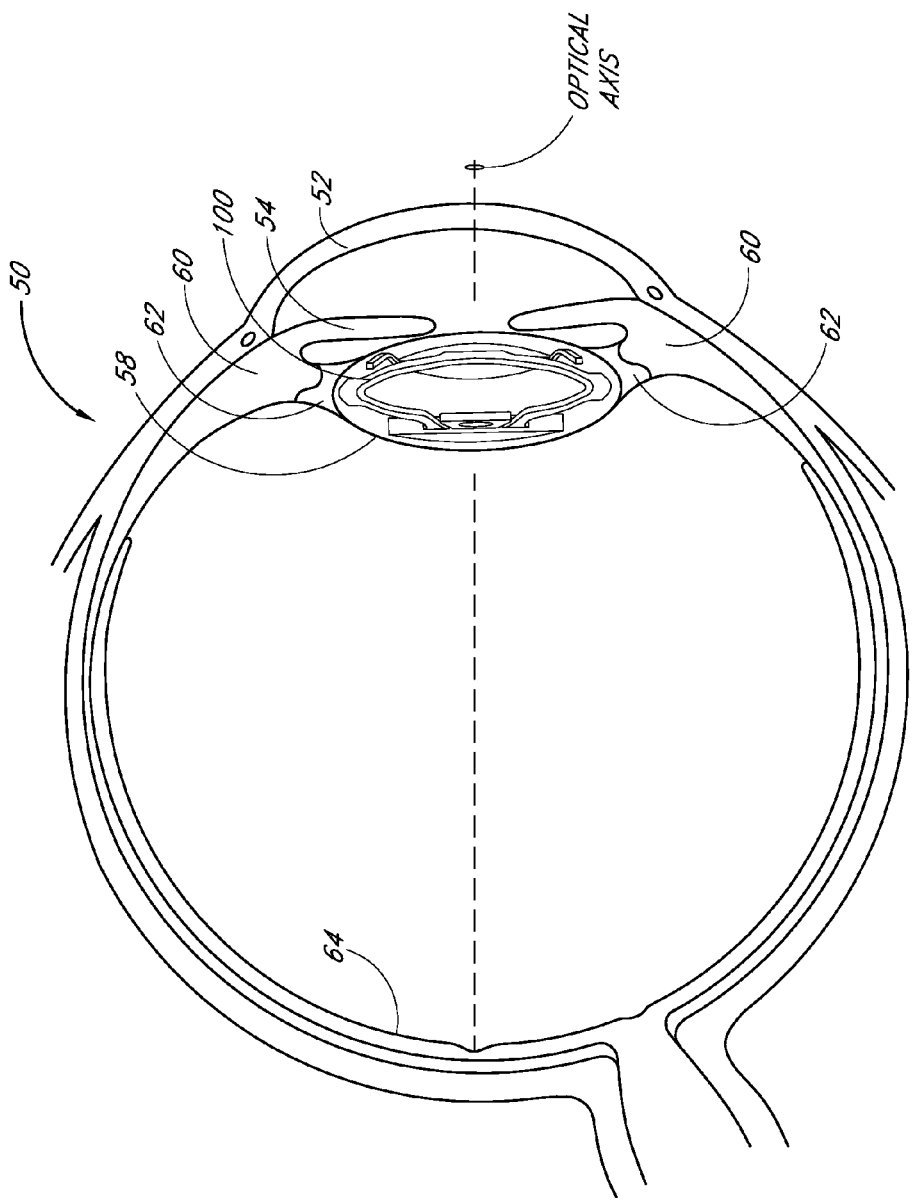
FIG. 16 is a sectional view of the human eye with the lens system implanted in the capsular bag and the lens system in the accommodated state.
Figure 17:
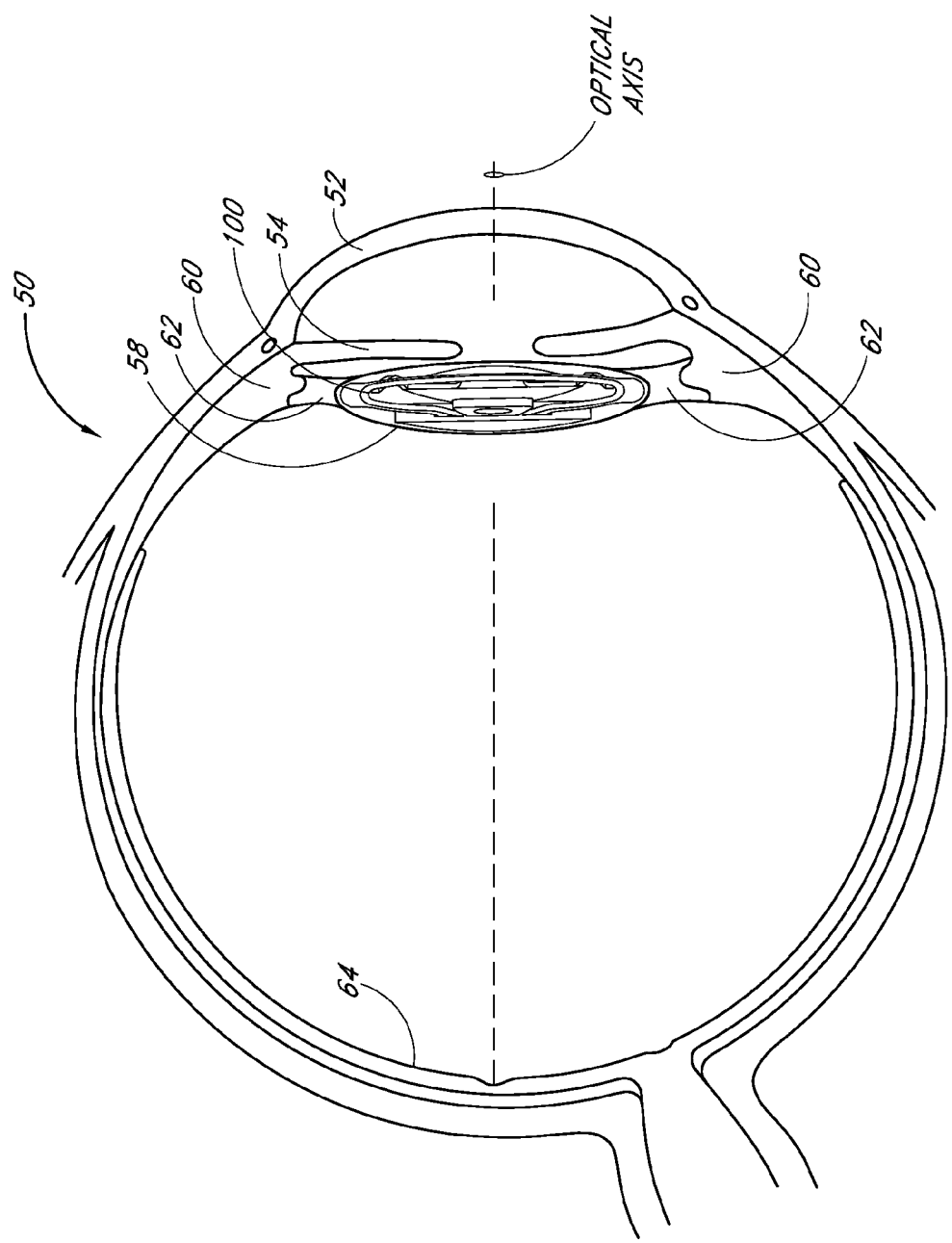
FIG. 17 is a sectional view of the human eye with the lens system implanted in the capsular bag and the lens system in the unaccommodated state.

As best seen in FIGS. 4, 5 and 7, the posterior portion 104 includes a posterior viewing element 118 and a posterior biasing element 120. The posterior biasing element 120 includes a first posterior translation member 122 extending from the posterior viewing element 118 to the first apex 112 and a second posterior translation member 124 extending from the posterior viewing element 118 to the second apex 116. In the illustrated embodiment, the first posterior translation member comprises a right arm 122a and a left arm 122b. Likewise, the depicted second posterior translation member 124 comprises a right arm 124a and a left arm 124b. However, in other embodiments either or both of the first and second posterior translation members 122, 124 may comprise a single arm or member, or more than two arms or members.

In the embodiment shown in FIG. 4, the anterior biasing element 108 and the posterior biasing element are configured symmetrically with respect to the plane A-A as the lens system 100 is viewed from the side. As used herein to describe the biasing elements 108, 120, "symmetric" or "symmetrically" means that, as the lens system 100 is viewed from the side, the first anterior translation member 110 and the first posterior translation member 122 extend from the first apex 112 at substantially equal first anterior and posterior biasing angles $\theta_1$, $\theta_2$ with respect to the line A-A (which, again, represents the edge of a plane which is substantially orthogonal to the optical axis and intersects the first and second apices 112, 116) and/or that the second anterior translation member 114 and the second posterior translation member 124 extend from the second apex 116 at substantially equal second anterior and posterior biasing angles $\theta_3$, $\theta_4$ with respect to the line A-A. Alternative or asymmetric configurations of the biasing elements are also possible. It should be further noted that a symmetric configuration of the biasing elements 108, 120 does not dictate symmetric positioning of the viewing elements with respect to the line A-A; in the embodiment shown in FIG. 4 the anterior viewing element 106 is closer to the line A-A than is the posterior viewing element.

Preferably, both the anterior viewing element 106 and the posterior viewing element 118 comprise an optic or lens having refractive power. (As used herein, the term "refractive" or "refractive power" shall include "diffractive" or "diffractive power".) Some preferred power ranges for the optics are discussed in detail below. In alternative embodiments one or both of the anterior and posterior viewing elements 106, 118 may comprise an optic with a surrounding or partially surrounding perimeter frame member or members, with some or all of the biasing elements/translation members attached to the frame member(s). As a further alternative, one of the viewing elements 106, 118 may comprise a perimeter frame with an open/empty central portion or void located on the optical axis, or a perimeter frame member or members with a zero-power lens or transparent member therein. In still further variations, one of the viewing elements 106, 118 may comprise only a zero-power lens or transparent member.

In one embodiment (see FIGS. 12, 19), a retention portion 126 is coupled to the anterior portion 102, preferably at the anterior viewing element 106. The retention portion 126 preferably includes a first retention member 128 and a second retention member 130, although in alternative embodiments the retention portion 126 may be omitted altogether, or may comprise only one retention member or more than two retention members. The first retention member 128 is coupled to the anterior viewing element 106 at a fixed end 128a and also includes a free end 128b opposite the fixed end 128a. Likewise, the second retention member 130 includes a fixed end 130a and a free end 130b. The retention members 128, 130 are illustrated as being coupled to the anterior viewing element 106 at the upper and lower edges thereof; however, the retention members 128, 130 may alternatively be attached to the anterior viewing element 106 at other suitable edge locations.

In one embodiment (see FIGS. 3, 5, 7-8, 18), the posterior portion 104 includes a distending portion 132, preferably attached to the posterior viewing element 118. A preferred distending portion 132 includes a first distending member 134 which in turn includes a fixed end 134a, a free end 134b opposite the fixed end 134a and preferably also includes an opening 134c formed therein. One preferred distending portion 132 also comprises a second distending member 136 with a fixed end 136a, a free end 136b and preferably an opening 136c formed therein. In alternative embodiments, the distending portion 132 may be omitted altogether, or may comprise a single distending member or more than two distending members. To optimize their effectiveness, a preferred location for the distending members 134, 136 is 90 degrees away (about the optical axis) from the apices 112, 116 on the posterior portion 104. Where the biasing elements form more than two apices (or where two apices are not spaced 180 degrees apart about the optical axis), one or more distending members may be positioned angularly midway between the apices about the optical axis. Alternatively, the distending member(s) may occupy other suitable positions relative to the apices (besides the "angularly midway" positions disclosed above); as further alternatives, the distending member(s) may be located on the anterior portion 102 of the lens system 100, or even on the apices themselves. The functions of the retention portion 126 and the distending portion 132 will be described in greater detail below.

III. The Lens System

Function/Optics

The anterior and posterior biasing elements 108, 120 function in a springlike manner to permit the anterior viewing element 106 and posterior viewing element 118 to move relative to each other generally along the optical axis. The biasing elements 108, 120 bias the viewing elements 106, 118 apart so that the elements 106, 108 separate to the accommodated position or accommodated state shown in FIG. 4. Thus, in the absence of any external forces, the viewing elements are at their maximum separation along the optical axis. The viewing elements 106, 118 of the lens system 100 may be moved toward each other, in response to a ciliary muscle force of up to 2 grams, to provide an unaccommodated position by applying appropriate forces upon the anterior and posterior portions 102, 104 and/or the apices 112, 116.

When the lens system 100 is implanted in the capsular bag 58 (FIGS. 16-17) the above described biasing forces cause the lens system 100 to expand along the optical axis so as to interact with both the posterior and anterior aspects of the capsular bag. Such interaction occurs throughout the entire range of motion of the ciliary muscle 60. At one extreme the ciliary muscle is relaxed and the zonules 62 pull the capsular bag 58 radially so as to cause the bag to become more disk shaped. The anterior and posterior sides of the bag, in turn, apply force to the anterior and posterior portions 102, 104 of the lens system 100, thereby forcing the viewing elements 106, 118 toward each other into the unaccommodated position. At the other extreme, the ciliary muscle contracts and the zonules 62 move inwardly to provide slack in the capsular bag 58 and allow the bag to become more football-shaped. The slack in the bag is taken up by the lens system due to the biasing-apart of the anterior and posterior viewing elements 106, 118. As the radial tension in the bag is reduced, the viewing elements 106, 118 move away from each other into an accommodated position. Thus, the distance between the viewing elements 106, 118 depends on the degree of contraction or relaxation of the ciliary muscle 60. As the distance between the anterior and posterior viewing elements 106, 118 is varied, the focal length of the lens system 100 changes accordingly. Thus, when the lens system 100 is implanted into the capsular bag (see FIGS. 16-17) the lens system 100 operates in conjunction with the natural accommodation processes of the eye to move between the accommodated (FIG. 16) and unaccommodated (FIG. 17) states in the same manner as would a healthy "natural" lens. Preferably, the lens system 100 can move between the accommodated and unaccommodated states in less than about one second.

The entire lens system 100, other than the optic(s), thus comprises an articulated frame whose functions include holding the optic(s) in position within the capsular bag and guiding and causing movement of the optic(s) between the accommodated and unaccommodated positions.

Advantageously, the entire lens system 100 may comprise a single piece of material, i.e. one that is formed without need to assemble two or more components by gluing, heat bonding, the use of fasteners or interlocking elements, etc. This characteristic increases the reliability of the lens system 100 by improving its resistance to material fatigue effects which can arise as the lens system experiences millions of accommodation cycles throughout its service life. It will be readily appreciated that the molding process and mold tooling discussed herein, lend themselves to the molding of lens systems 100 that comprise a single piece of material. However, any other suitable technique may be employed to manufacture single-piece lens systems.

In those embodiments where the optic(s) are installed into annular or other perimeter frame member(s) (see discussion below), the articulated frame may comprise a single piece of material, to obtain the performance advantages discussed above. It is believed that the assembly of the optic(s) to the articulated frame will not substantially detract from the achievement of these advantages.

The lens system 100 has sufficient dynamic range that the anterior and posterior viewing elements 106, 118 move about 0.5-4 mm, preferably about 1-3 mm, more preferably about 1-2 mm, and most preferably about 1.5 mm closer together when the lens system 100 moves from the accommodated state to the unaccommodated state. In other words the separation distance X (see FIGS. 9-10, 14-15) between the anterior and posterior viewing elements 106, 118, which distance may for present purposes be defined as the distance along the optical axis (or a parallel axis) between a point of axial intersection with the posterior face of the anterior viewing element 106 and a point of axial intersection with the anterior face of the posterior viewing element 118, decreases by the amount (s) disclosed above upon movement of the lens system 100 to the unaccommodated state. Simultaneously, in one preferred mode the total system thickness Y decreases from about 3.0-4.0 mm in the accommodated state to about 1.5-2.5 mm in the unaccommodated state.

Figure 6:
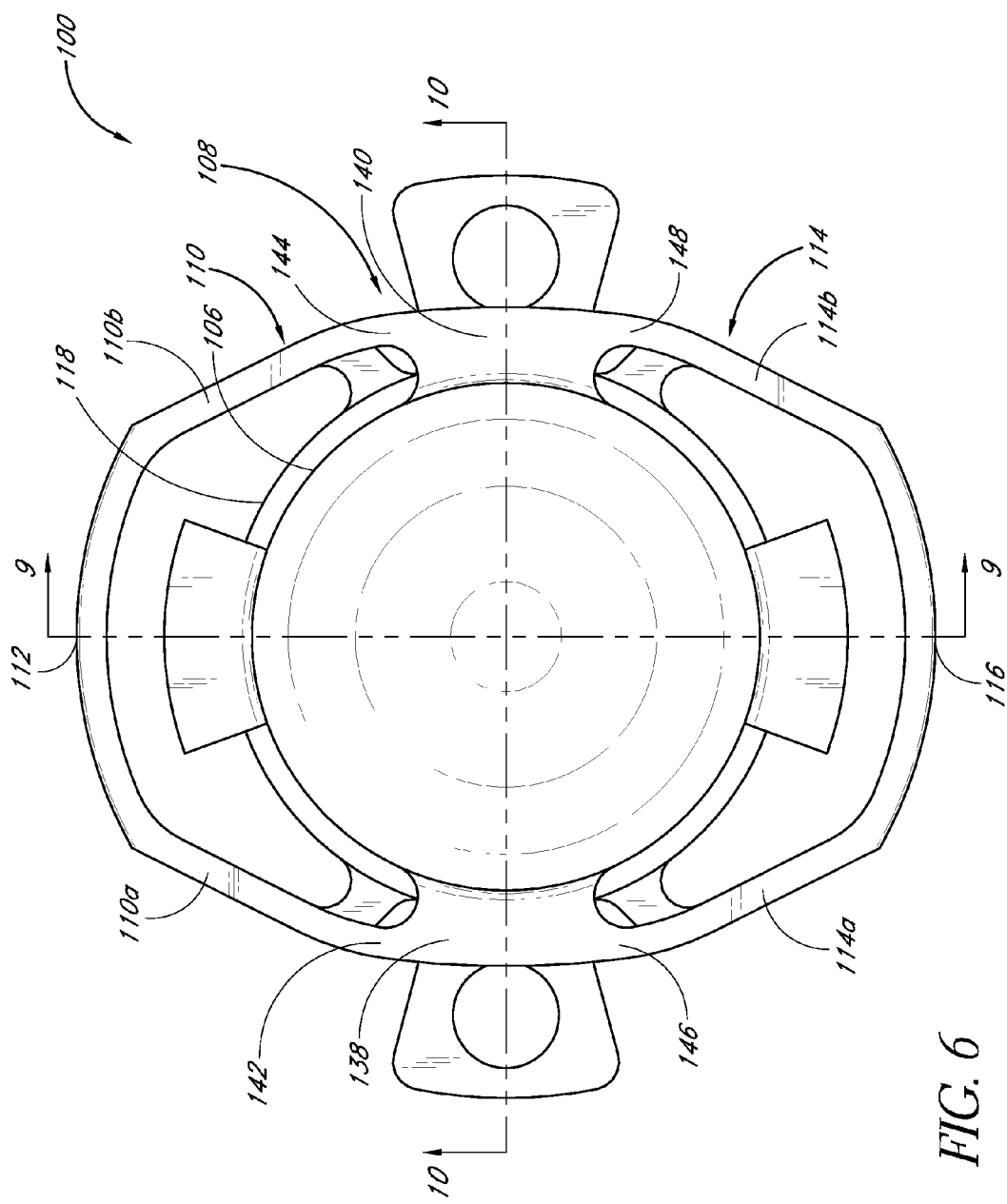
FIG. 6 is a front view of the lens system.

As may be best seen in FIG. 6, the first anterior translation member 110 connects to the anterior viewing element 106 via connection of the left and right arms 110a, 110b to first and second transition members 138, 140 at attachment locations 142, 144. The second anterior translation member 114 connects to the anterior viewing element 106 via connection of left and right arms 114a, 114b to the first and second transition members 138, 140 at attachment locations 146, 148. This is a presently preferred arrangement for the first and second anterior translation members 110, 114; alternatively, the first and second anterior translation members 110, 114 could be connected directly to the anterior viewing element 106, as is the case with the connection of the first and second posterior translation members 122, 124 to the posterior viewing element 118.

However the connection is established between the first and second anterior translation members 110, 114 and the anterior viewing element 106, it is preferred that the attachment locations 142, 144 corresponding to the first anterior translation member 110 be farther away from the first apex 112 than is the closest edge or the periphery of the anterior viewing element 106. This configuration increases the effective length of the first anterior translation member 110/arms 110a, 110b, in comparison to a direct or straight attachment between the apex 112 and the nearest/top edge of the anterior viewing element 106. For the same reasons, it is preferred that the attachment locations 146, 148 associated with the second anterior translation member 114 be farther away from the second apex 116 than is the closest/bottom edge of the anterior viewing element 106.

As best seen in FIG. 7, the first posterior translation member 122 is preferably connected directly to the posterior viewing element 118 via attachment of the left and right arms 122a, 122b to the element 118 at attachment points 150, 152. Likewise, the second posterior translation member 124 is preferably directly connected to the posterior viewing element 118 via connection of the left and right arms 124a, 124b to the element 118 at attachment points 154, 156, respectively. In alternative embodiments, the first and second posterior translation members 124, 122 can be connected to the posterior viewing element via intervening members as is done with the anterior viewing element 106. No matter how these connections are made, it is preferred that the attachment locations 150, 152 be spaced further away from the first apex 112 than is the nearest edge or the periphery of the posterior viewing element 118. Similarly, it is preferred that the attachment locations 154, 156 be spaced further away from the second apex 116 than is the closest edge of the posterior viewing element 118.

By increasing the effective length of some or all of the translation members 110, 114, 122, 124 (and that of the arms 110a, 110b, 114a, 114b, 122a, 122b, 124a, 124b where such structure is employed), one preferred configuration of the attachment locations 142, 144, 146, 148, 150, 152, 154, 156 relative to the first and second apices 112, 116 enables the anterior and/or posterior viewing elements 106, 118 to move with respect to one another a greater distance along the optical axis, for a given angular displacement of the anterior and/or posterior translation members. This arrangement thus facilitates a more responsive spring system for the lens system 100 and minimizes material fatigue effects associated with prolonged exposure to repeated flexing.

In the illustrated embodiment, the attachment location 142 of the first anterior translation member 110 is spaced from the corresponding attachment location 146 of the second anterior translation member 114 along the periphery of the anterior viewing element, and the same relationship exists between the other pairs of attachment locations 144, 148; 150, 154; and 152, 156. This arrangement advantageously broadens the support base for the anterior and posterior viewing elements 106, 118 and prevents them from twisting about an axis parallel to the lateral axis, as the viewing elements move between the accommodated and unaccommodated positions.

It is also preferred that the attachment locations 142, 144 of the first anterior translation member 110 be located equidistant from the first apex 112, and that the right and left arms 110a, 110b of the member 110 be equal in length. Furthermore, the arrangement of the attachment locations 146, 148, arms 114a, 114b and second apex preferably mirrors that recited above regarding the first anterior translation member 110, while the apices 112, 116 are preferably equidistant from the optical axis and are situated 180 degrees apart. This configuration maintains the anterior viewing element 106 orthogonal to the optical axis as the viewing element 106 moves back and forth and the anterior viewing element flexes.

For the same reasons, a like combination of equidistance and equal length is preferred for the first and second posterior translation members 122, 124 and their constituent arms 122a, 122b, 124a, 124b and attachment points 150, 152, 154, 156, with respect to the apices 112, 116. However, as shown the arms 122a, 122b, 124a, 124b need not be equal in length to their counterparts 110a, 110b, 114a, 114b in the first and second anterior translation members 110, 114.

Where any member or element connects to the periphery of the anterior or posterior viewing elements 106, 118, the member defines a connection geometry or attachment area with a connection width W and a connection thickness T (see FIG. 4 and the example illustrated therein, of the connection of the second posterior translation member 124 to the posterior viewing element 118). For purposes of clarity, the connection width is defined as being measured along a direction substantially parallel to the periphery of the viewing element in question, and the connection thickness is defined as measured along a direction substantially perpendicular to the periphery of the viewing element. (The periphery itself is deemed to be oriented generally perpendicular to the optical axis as shown in FIG. 4.) Preferably, no attachment area employed in the lens system 100 has a ratio of width to thickness less than 3. It has been found that such a geometry reduces distortion of the viewing element/optic due to localized forces. For the same reasons, it is also preferred that each of the translation members 110, 114, 122, 124 be connected to the periphery of the respective viewing elements at two or more attachment areas, each having a preferred geometry discussed above.

A number of suitable cross-sectional configurations may be used along some or all of the length of the translation members and/or arms 110a, 110b, 114a, 114b, 122a, 122b, 124a, 124b. The shape preferably is defined by a relatively broad and flat or slightly curved outer surface. It is intended that when in use the outer surface faces away from the interior of the lens system and/or toward the capsular bag 58. The remaining surfaces, proportions and dimensions making up the cross-sectional shape can vary widely but may advantageously be selected to facilitate manufacture of the lens system 100 via molding or casting techniques while minimizing stresses in the arms during use of the lens system.

It is further contemplated that the dimensions, shapes, and/or proportions of the cross-sectional configuration of the translation members and/or arms 110a, 110b, 114a, 114b, 122a, 122b, 124a, 124b may vary along the length of the members/arms. This may be done in order to, for example, add strength to high-stress regions of the arms, fine-tune their spring characteristics, add rigidity or flexibility, etc.

As discussed above, each of the anterior viewing element 106 and the posterior viewing element 118 preferably comprises an optic having refractive power. In one preferred embodiment, the anterior viewing element 106 comprises a biconvex lens having positive refractive power and the posterior viewing element 118 comprises a convexo-concave lens having negative refractive power. The anterior viewing element 106 may comprise a lens having a positive power advantageously less than 55 diopters, preferably less than 40 diopters, more preferably less than 35 diopters, and most preferably less than 30 diopters. The posterior viewing element 118 may comprise a lens having a power which is advantageously between −25 and 0 diopters, and preferably between −25 and −15 diopters. In other embodiments, the posterior viewing element 118 comprises a lens having a power which is between −15 and 0 diopters, preferably between −13 and −2 diopters, and most preferably between −10 and −5 diopters. Advantageously, the total power of the optic(s) employed in the lens system 100 is about 5-35 diopters; preferably, the total power is about 10-30 diopters; most preferably, the total power is about 15-25 diopters. (As used herein, the term "diopter" refers to lens or system power as measured when the lens system 100 has been implanted in the human eye in the usual manner.) It should be noted that if materials having a high index of refraction (e.g., higher than that of silicone) are used, the optics may be made thinner which facilitates a wider range of motion for the optics. This in turn allows the use of lower-power optics than those specified above. In addition, higher-index materials allow the manufacture of a higher-power lens for a given lens thickness and thereby reduce the range of motion needed to achieve a given range of accommodation.

Some lens powers and radii of curvature presently preferred for use with an embodiment of the lens system 100 with optic(s) having a refractive index of about 1.432 are as follows: a +31 diopter, biconvex lens with an anterior radius of curvature of 5.944 mm and a posterior radius of curvature of 5.944 mm; a +28 diopter, biconvex lens with an anterior radius of curvature of 5.656 mm and a posterior radius of curvature of 7.788 mm; a +24 diopter, biconvex lens with an anterior radius of curvature of 6.961 mm and a posterior radius of curvature of 8.5 mm; a −10 diopter, biconcave lens with an anterior radius of curvature of 18.765 mm and a posterior radius of curvature of 18.765 mm, a −8 diopter, concavo-convex lens with an anterior radius of curvature of between 9 mm and 9.534 mm and a posterior radius of curvature of 40 mm, and a −5 diopter, concavo-convex lens with an anterior radius of curvature of between 9 mm and 9.534 mm and a posterior radius of curvature of 20 mm. In one embodiment, the anterior viewing element comprises the +31 diopter lens described above and the posterior viewing element comprises the −10 diopter lens described above. In another embodiment, the anterior viewing element comprises the +28 diopter lens described above and the posterior viewing element comprises the −8 diopter lens described above. In another embodiment, the anterior viewing element comprises the +24 diopter lens described above and the posterior viewing element comprises the −5 diopter lens described above.

The combinations of lens powers and radii of curvature specified herein advantageously minimize image magnification. However, other designs and radii of curvature provide modified magnification when desirable.

The lenses of the anterior viewing element 106 and the posterior viewing element 118 are relatively moveable as discussed above; advantageously, this movement is sufficient to produce an accommodation of at least one diopter, preferably at least two diopters and most preferably at least three diopters. In other words, the movement of the optics relative to each other and/or to the cornea is sufficient to create a difference between (i) the refractive power of the user's eye in the accommodated state and (ii) the refractive power of the user's eye in the unaccommodated state, having a magnitude expressed in diopters as specified above. Where the lens system 100 has a single optic, the movement of the optic relative to the cornea is sufficient to create a difference in focal power as specified above.

Advantageously, the lens system 100 can be customized for an individual patient's needs by shaping or adjusting only one of the four lens faces, and thereby altering the overall optical characteristics of the system 100. This in turn facilitates easy manufacture and maintenance of an inventory of lens systems with lens powers which will fit a large population of patients, without necessitating complex adjustment procedures at the time of implantation. It is contemplated that all of the lens systems in the inventory have a standard combination of lens powers, and that a system is fitted to a particular patient by simply shaping only a designated "variable" lens face. This custom-shaping procedure can be performed to-order at a central manufacturing facility or laboratory, or by a physician consulting with an individual patient. In one embodiment, the anterior face of the anterior viewing element is the designated sole variable lens face. In another embodiment, the anterior face of the posterior viewing element is the only variable face. However, any of the lens faces is suitable for such designation. The result is minimal inventory burden with respect to lens power (all of the lens systems in stock have the same lens powers) without requiring complex adjustment for individual patients (only one of the four lens faces is adjusted in the fitting process).

IV. The Lens System

Distending Portion

Figure 18:
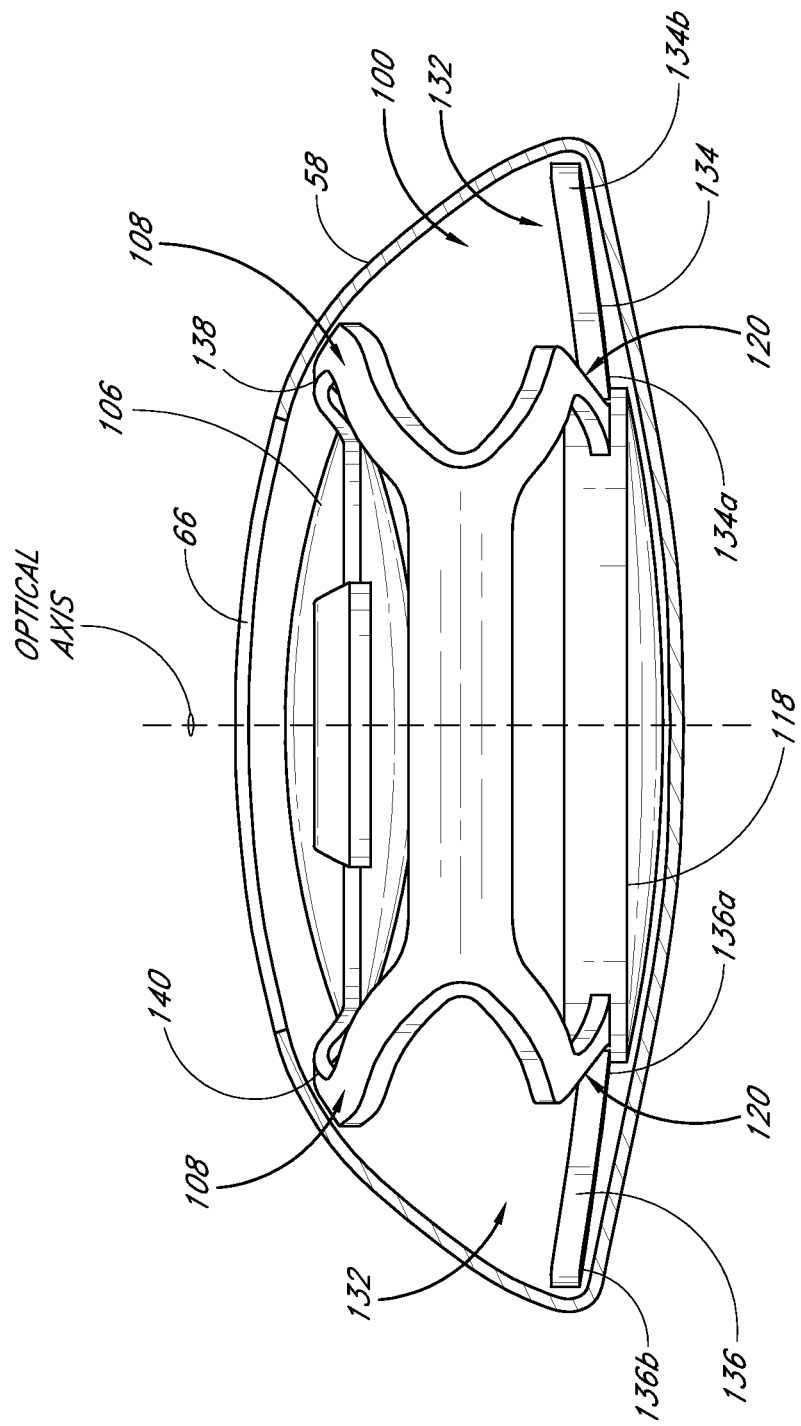
FIG. 18 is a partial top sectional view of another embodiment of the lens system, implanted in the capsular bag.

FIG. 18 depicts the function of the distending portion 132 in greater detail. The lens system 100 is shown situated in the capsular bag 58 in the customary manner with the anterior viewing element 106 and posterior viewing element 118 arranged along the optical axis. The capsular bag 58 is shown with a generally circular anterior opening 66 which may often be cut into the capsular bag during installation of the lens system 100. The first and second distending members 134, 136 of the distending portion 132 distend the capsular bag 58 so that intimate contact is created between the posterior face of the posterior viewing element and/or the posterior biasing element 120. In addition, intimate contact is facilitated between the anterior face of the anterior viewing element 106 and/or anterior biasing element 108. The distending members 134, 136 thus remove slack from the capsular bag 58 and ensure optimum force coupling between the bag 58 and the lens system 100 as the bag 58 is alternately stretched and released by the action of the ciliary muscle.

Furthermore, the distending members 134, 136 reshape the capsular bag 58 into a taller, thinner configuration along its range of accommodation to provide a wider range of relative motion of the viewing elements 106, 118. When the capsular bag 58 is in the unaccommodated state, the distending members 134, 136 force the capsular bag into a thinner configuration (as measured along the optical axis) in comparison to the unaccommodated configuration of the capsular bag 58 with the natural lens in place. Preferably, the distending members 134, 136 cause the capsular bag 58 to take on a shape in the unaccommodated state which is about 1.0-2.0 mm thinner, more preferably about 1.5 mm thinner, along the optical axis than it is with the natural lens in place and in the unaccommodated state.

With such a thin "starting point" provided by the distending members 134, 136, the viewing elements 106, 118 of the lens system can move a greater distance apart, and provide a greater range of accommodation, without causing undesirable contact between the lens system and the iris. Accordingly, by reshaping the bag as discussed above the distending members 134, 136 facilitate a range of relative motion of the anterior and posterior viewing elements 106, 118 of about 0.5-4 mm, preferably about 1-3 mm, more preferably about 1-2 mm, and most preferably about 1.5 mm.

The distending portion 132/distending members 134, 136 are preferably separate from the anterior and posterior biasing elements 108, 120; the distending members 134, 136 thus preferably play no part in biasing the anterior and posterior viewing elements 106, 118 apart toward the accommodated position. This arrangement is advantageous because the apices 112, 116 of the biasing elements 108, 120 reach their point of minimum protrusion from the optical axis (and thus the biasing elements reach their minimum potential effectiveness for radially distending the capsular bag) when the lens system 100 is in the accommodated state (see FIG. 16), which is precisely when the need is greatest for a taut capsular bag so as to provide immediate response to relaxation of the ciliary muscles. One preferred distending portion is "static" (as opposed to the "dynamic" biasing members 108, 120 which move while urging the viewing elements 106, 118 to the accommodated position or carrying the viewing elements to the unaccommodated position) in that its member(s) protrude a substantially constant distance from the optical axis throughout the range of motion of the viewing elements 106, 118. Although some degree of flexing may be observed in the distending members 134, 136, they are most effective when rigid. Furthermore, the thickness and/or cross-sectional profile of the distending members 134/136 may be varied over the length of the members as desired to provide a desired degree of rigidity thereto.

The distending portion 132/distending members 134, 136 advantageously reshape the capsular bag 58 by stretching the bag 58 radially away from the optical axis and causing the bag 58 to take on a thinner, taller shape throughout the range of accommodation by the eye. This reshaping is believed to facilitate a broad (as specified above) range of relative motion for the viewing elements of the lens system 100, with appropriate endpoints (derived from the total system thicknesses detailed above) to avoid the need for unacceptably thick optic (s) in the lens system.

If desired, the distending members 134, 136 may also function as haptics to stabilize and fixate the orientation of the lens system 100 within the capsular bag. The openings 134c, 136c of preferred distending members 134,136 permit cellular ingrowth from the capsular bag upon positioning of the lens system 100 therein. Finally, other methodologies, such as a separate capsular tension ring or the use of adhesives to glue the capsular bag together in selected regions, may be used instead of or in addition to the distending portion 132, to reduce "slack" in the capsular bag.

A tension ring can also act as a physical barrier to cell growth on the inner surface of the capsular bag, and thus can provide additional benefits in limiting posterior capsule opacification, by preventing cellular growth from advancing posteriorly on the inner surface of the bag. When implanted, the tension ring firmly contacts the inner surface of the bag and defines a circumferential barrier against cell growth on the inner surface from one side of the barrier to another.

Figure 19:
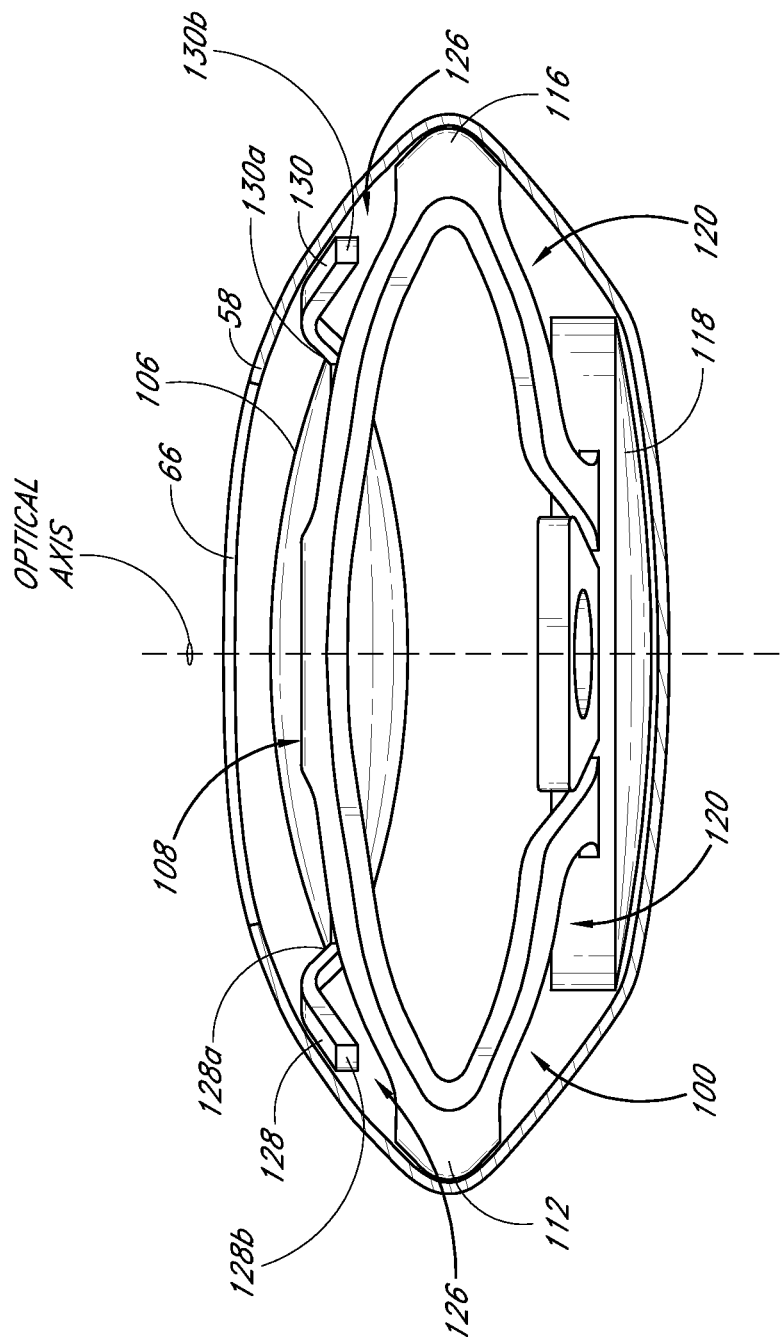
FIG. 19 is a partial side sectional view of another embodiment of the lens system, implanted in the capsular bag.

FIG. 19 shows the function of the retention portion 126 in greater detail. It is readily seen that the first and second retention members 128, 130 facilitate a broad contact base between the anterior portion of the lens system 100 and the anterior aspect of the capsular bag 58. By appropriately spacing the first and second retention members 128, 130, the members prevent extrusion of the anterior viewing element 106 through the anterior opening 66. It is also readily seen that where contact occurs between the anterior aspect of the capsular bag 58 and one or both of the retention members 128, 130, the retention members also participate in force coupling between the bag 58 and the lens system 100 as the bag is stretched and released by the action of the ciliary muscles.

As best seen in FIGS. 18 and 19, the anterior portion 102 of the lens system 100 forms a number of regions of contact with the capsular bag 58, around the perimeter of the anterior viewing element 106. In the illustrated embodiment, at least some of these regions of contact are located on the anteriormost portions of the anterior biasing element 108, specifically at the transition members 138, 140, and at the retention members 128, 130. The transition members and the retention members define spaces therebetween at the edges of the anterior viewing element 106 to permit fluid to flow between the interior of the capsular bag 58 and the portions of the eye anterior of the bag 58. In other words, the anterior portion of the lens system 100 includes at least one location which is spaced from and out of contact with the capsular bag 58 to provide a fluid flow channel extending from the region between the viewing elements 106, 118 to the exterior of the bag 58. Otherwise, if the anterior portion 102 of the lens system 100 seals the anterior opening 66 of the bag 58, the resulting prevention of fluid flow can cause the aqueous humor in the capsular bag to stagnate, leading to a clinically adverse event, and can inhibit the movement of the lens system 100 between the accommodated and unaccommodated states.

If desired, one or both of the retention members 128, 130 may have an opening 129 formed therein to permit fluid flow as discussed above.

The retention members 128, 130 and the transition members 138, 140 also prevent contact between the iris and the anterior viewing element 106, by separating the anterior opening 66 from the anterior face of the viewing element 106. In other words, the retention members 128, 130 and the transition members 138, 140 displace the anterior aspect of the capsular bag 58, including the anterior opening 66, anteriorly from the anterior viewing element 106, and maintain this separation throughout the range of accommodation of the lens system. Thus, if contact occurs between the iris and the lens system-capsular bag assembly, no part of the lens system will touch the iris, only the capsular bag itself, in particular those portions of the bag 58 overlying the retention members 128, 130 and/or the transition members 138, 140. The retention members 128, 130 and/or the transition members 138, 140 therefore maintain a separation between the iris and the lens system, which can be clinically adverse if the contacting portion(s) of the lens system are constructed from silicone.

V. The Lens System

Stop Members

Figure 20:
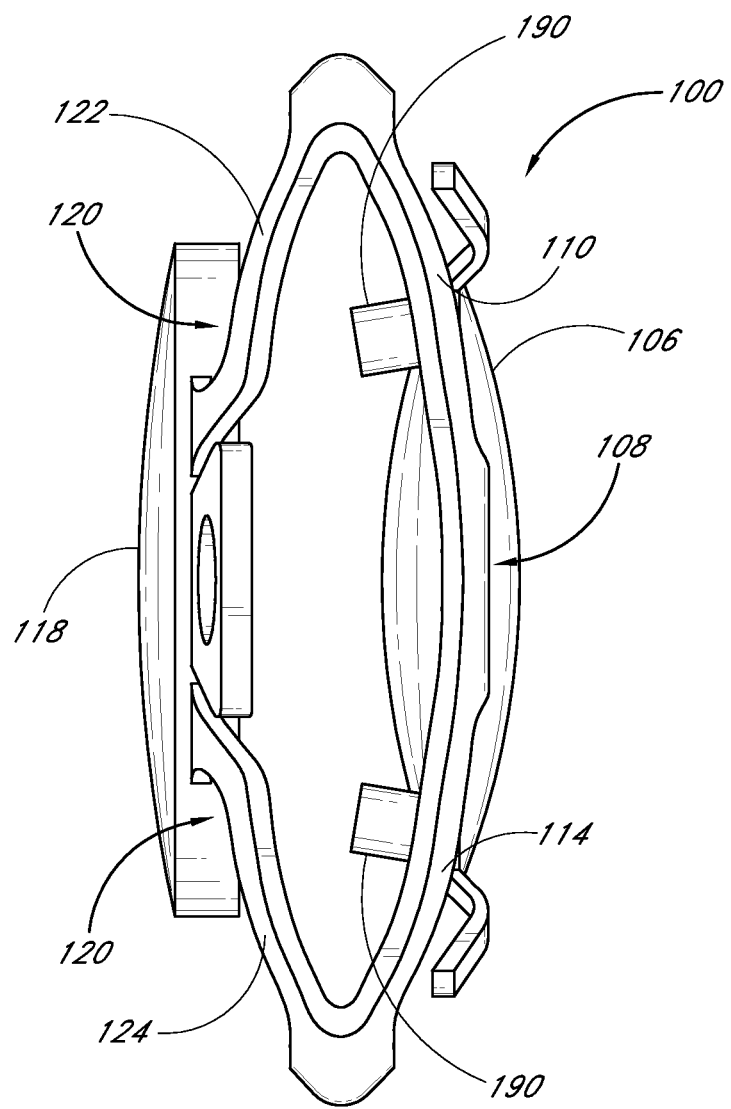
FIG. 20 is a side view of a stop member system employed in one embodiment of the lens system.
Figure 21:
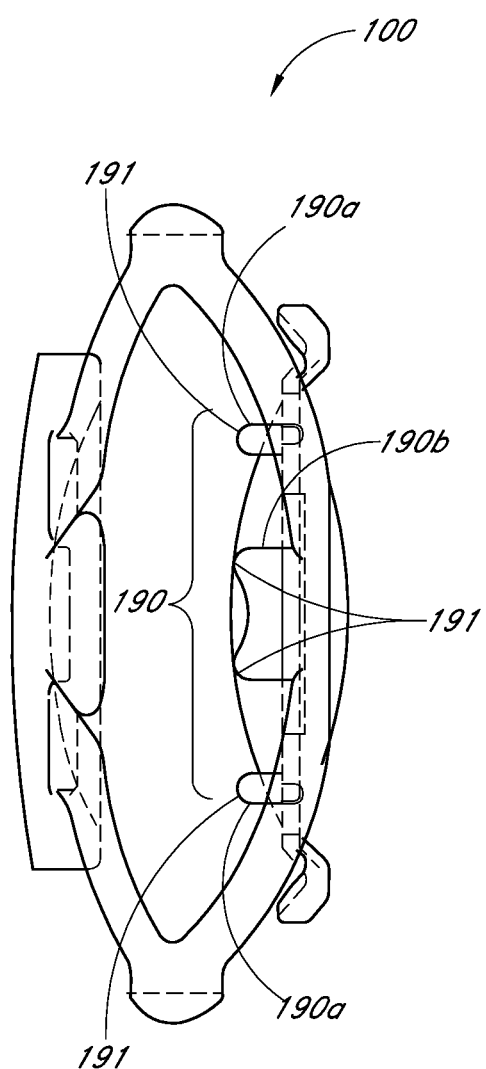
FIG. 21 is a side elevation view of another embodiment of the lens system with a number of separation members.
Figure 22:
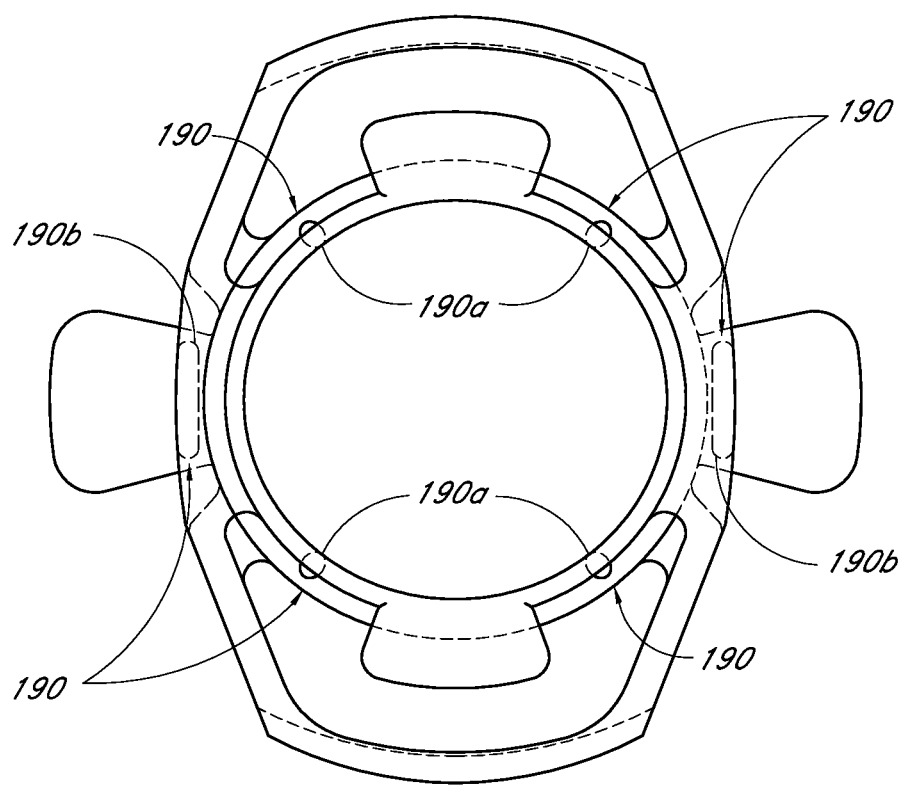
FIG. 22 is a front elevation view of the lens system of FIG. 21.
Figure 23:
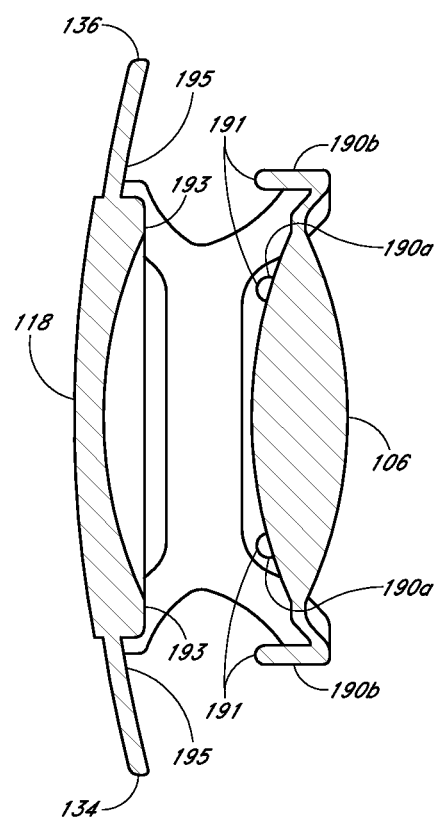
FIG. 23 is an overhead sectional view of the lens system of FIG. 21.
Figure 24:
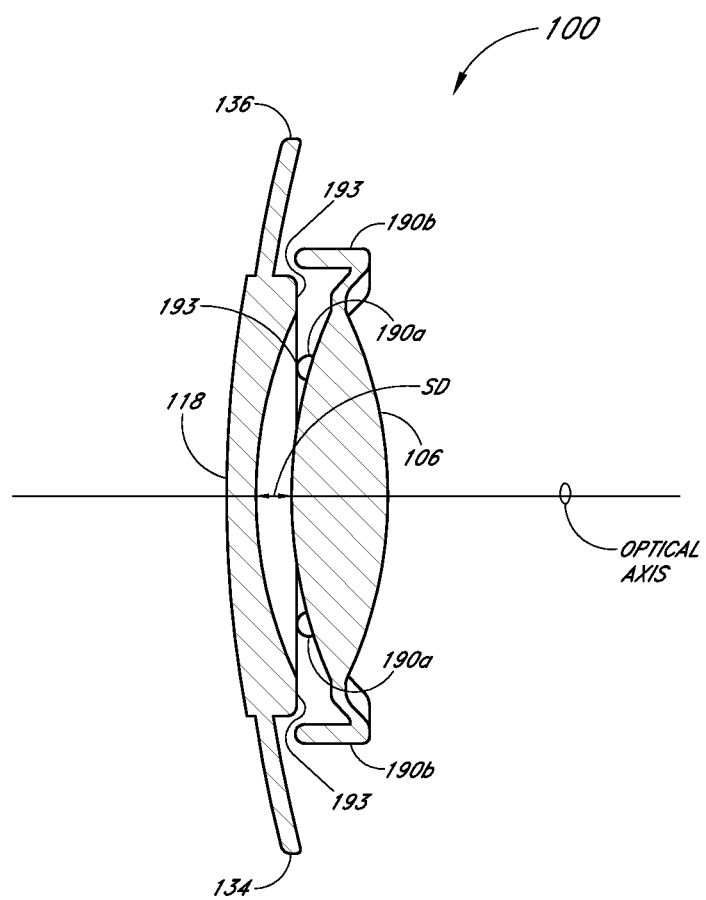
FIG. 24 is an overhead sectional view of the lens system of FIG. 21, with the viewing elements at a minimum separation distance.

As depicted in FIG. 20, one or more stop members or separation members 190 may be located where appropriate on the anterior and/or posterior biasing elements 108, 120 to limit the convergent motion of the anterior and posterior viewing elements 106, 118, and preferably prevent contact therebetween. As the lens system 100 moves toward the unaccommodated position, the stop member(s) located on the anterior biasing element 108 come into contact with the posterior biasing element 120 (or with additional stop member(s) located thereon), and any stop member(s) located on the posterior biasing element 120 come into contact with the anterior biasing element 108 (or with additional stop member(s) located thereon). The stop members 190 thus define a point or state of maximum convergence (in other words, the unaccommodated state) of the lens system 100/viewing elements 106, 118. Such definition advantageously assists in setting one extreme of the range of focal lengths which the lens system may take on (in those lens systems which include two or more viewing elements having refractive power) and/or one extreme of the range of motion of the lens system 100.

The stop members 190 shown in FIG. 20 are located on the first and second anterior translation members 110, 114 of the anterior biasing element 108 and extend posteriorly therefrom. When the anterior and posterior viewing elements 106, 118 move together, one or more of the stop members 190 will contact the posterior translation member(s) 122, 124, thereby preventing further convergent motion of the viewing elements 106, 118. Of course, in other embodiments the stop member(s) 190 can be in any suitable location on the lens system 100.

FIGS. 21-25 depict another embodiment of the lens system 100 having a number of stop members or separation members 190. In this embodiment the stop members 190 include posts 190a and tabs 190b, although it will be apparent that any number or combination of suitable shapes may be employed for the stop members 190. Each of the stop members 190 has at least one contact surface 191, one or more of which abuts an opposing surface of the lens system 100 when the anterior and posterior viewing elements 106, 118 converge to a minimum separation distance SD (see FIG. 24). In the embodiment shown, one or more of the contact surfaces 191 of the posts 190a are configured to abut an opposing surface defined by a substantially flat anterior perimeter portion 193 of the posterior viewing element 118, when the viewing elements 106, 118 are at the minimum separation distance SD. One or more of the contact surfaces 191 of the tabs 190b are configured to abut opposing surfaces defined by substantially flat anterior faces 195 of the distending members 134, 136, only if the viewing elements 106, 118 are urged together beyond the minimum separation distance SD. This arrangement permits the tabs 190b to function as secondary stop members should the posts 190a fail to maintain separation of the viewing elements.

In other embodiments all of the contact surfaces 191 of the posts 190a and tabs 190b may be configured to contact their respective opposing surfaces when the viewing elements 106, 118 are at the minimum separation distance SD. In still further embodiments, the contact surfaces 191 of the tabs 190b may be configured to contact the opposing surfaces when the viewing elements 106, 118 are at the minimum separation distance SD and the contact surfaces 191 of the posts 190a configured to contact the opposing surfaces only if the viewing elements 106, 118 are urged together beyond the minimum separation distance SD. In one embodiment, the minimum separation distance SD is about 0.1-1.0 mm; in another embodiment the minimum separation distance SD is about 0.5 mm.

Figure 25:
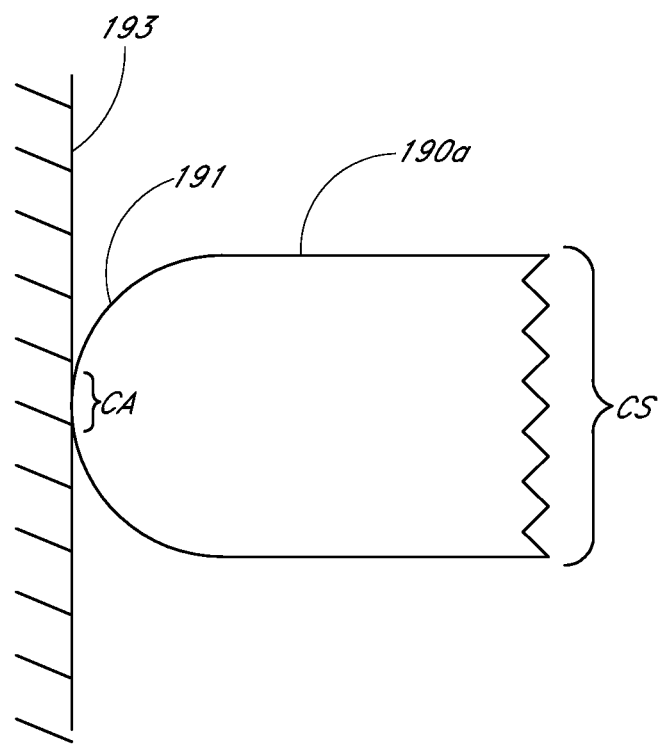
FIG. 25 is a closeup view of the contact between a separation member and an opposing surface.

When one of the contact surfaces abuts one of the opposing surfaces, the two surfaces define a contact area CA (see FIG. 25, depicting an example of a contact area CA defined when the contact surface 191 of a post 190a contacts an opposing surface defined by the perimeter portion 193 of the posterior viewing element 118). Preferably, the contact surface and opposing surface are shaped to cooperatively minimize the size of the contact area, to prevent adhesion between the contact surface and the opposing surface, which is often a concern when one or both of these surfaces has an adhesive affinity for the other. In the embodiment shown, this non-adhesive characteristic is achieved by employing a substantially hemispherical contact surface 191 and a substantially flat opposing surface (perimeter portion 193). Of course, other configurations can be selected for the contact surface(s) 191, including conical, frustoconical, hemicylindrical, pyramidal, or other rounded, tapered or pointed shapes. All of these configurations minimize the contact area CA while permitting the cross-sectional area CS of the stop member 190 (such as the post 190a depicted) to be made larger than the contact area CA, to impart sufficient strength to the stop member despite the relatively small contact area CA. Indeed, when constructing the contact surface(s) 191 any configuration may be employed which defines a contact area CA which is smaller than the cross-sectional area CS of the stop member 190. As further alternatives, the contact surface(s) 191 may be substantially flat and the opposing surface(s) may have a shape which defines, upon contact with the opposing surface, a contact area CA which is smaller than the cross-sectional area CS of the stop member. Thus, the opposing surface(s) may have, for example, a hemispherical, conical, frustoconical, hemicylindrical, pyramidal, or other rounded, tapered or pointed shape.

Other design features of the stop members 190 can be selected to maximize their ability to prevent adhesion of the contact surface(s) to the corresponding opposing surface(s), or adhesion to each other of any part of the anterior and posterior portions 102, 104 of the lens system 100. For example, the contact and opposing surfaces may be formed from dissimilar materials to reduce the effect of any self-adhesive materials employed in forming the lens system 100. In addition the shape and/or material employed in constructing one or more of the stop members 190 can be selected to impart a spring-like quality to the stop member(s) in question, so that when the stop member is loaded in compression as the viewing elements are urged together at the minimum separation distance, the stop member tends to exert a resisting spring force, due to either bending or axial compression (or both) of the stop member, which in turn derive from the elasticity of the material(s) from which the stop member is constructed, or the shape of the stop member, or both. This springlike quality is particularly effective for inhibiting adhesion of areas of the anterior and posterior portions 102, 104 other than the contact surface(s) and opposing surface(s).

As used herein, the term "adhesion" refers to attachment to each other of (i) an area of the anterior portion 102 of the lens system 100 and (ii) a corresponding area of the posterior portion 104 (other than the apices 112, 116), wherein such attachment is sufficiently strong to prevent, other than momentarily, the anterior and posterior viewing elements 106, 118 from moving apart along the optical axis under the biasing force of the anterior and/or posterior biasing elements 108, 120. If the areas in question are formed of different materials, adhesion may occur where at least one of the materials has an adhesive affinity for the other material. If the areas in question are formed of the same material, adhesion may occur where the material has an adhesive affinity for itself.

In the embodiment shown, four posts 190a are positioned near the perimeter of the anterior viewing element 106, equally angularly spaced around the optical axis. In addition, two tabs 190b are located on either side of the anterior viewing element, midway between the apices 112, 116 of the lens system. Naturally, the number, type and/or position of the stop members 190 can be varied while preserving the advantageous function of maintaining separation between the anterior and posterior portions of the lens system.

The illustrated embodiment employs stop members 190 which extend posteriorly from the anterior portion 102 of the lens system 100, so that the contact surfaces 191 are located on the posterior extremities of the stop members 190 and are configured to abut opposing surfaces formed on the posterior portion 104 of the lens system 100. However, it will be appreciated that some or all of the stop members 190 may extend anteriorly from the posterior portion 104 of the lens system 100, so that their contact surfaces 191 are located on the anterior extremities of the stop members 190 and are configured to abut opposing surfaces formed on the anterior portion 102 of the lens system 100.

Additional features and embodiments of lens systems are described in U.S. patent application Ser. No. 10/020,853 (filed Dec. 11, 2001) and Ser. No. 10/207,708 (filed Jul. 25, 2002), which are hereby incorporated by reference herein in their entireties.

VI. The Lens System

Additional Embodiments

FIGS. 26-37 depict additional embodiments of the intraocular lens. In the illustrated embodiments, the lens systems have distending portions 132 and retention portions 126 for positioning the lens systems in particular configurations within the capsular bag 58.

Figure 26:
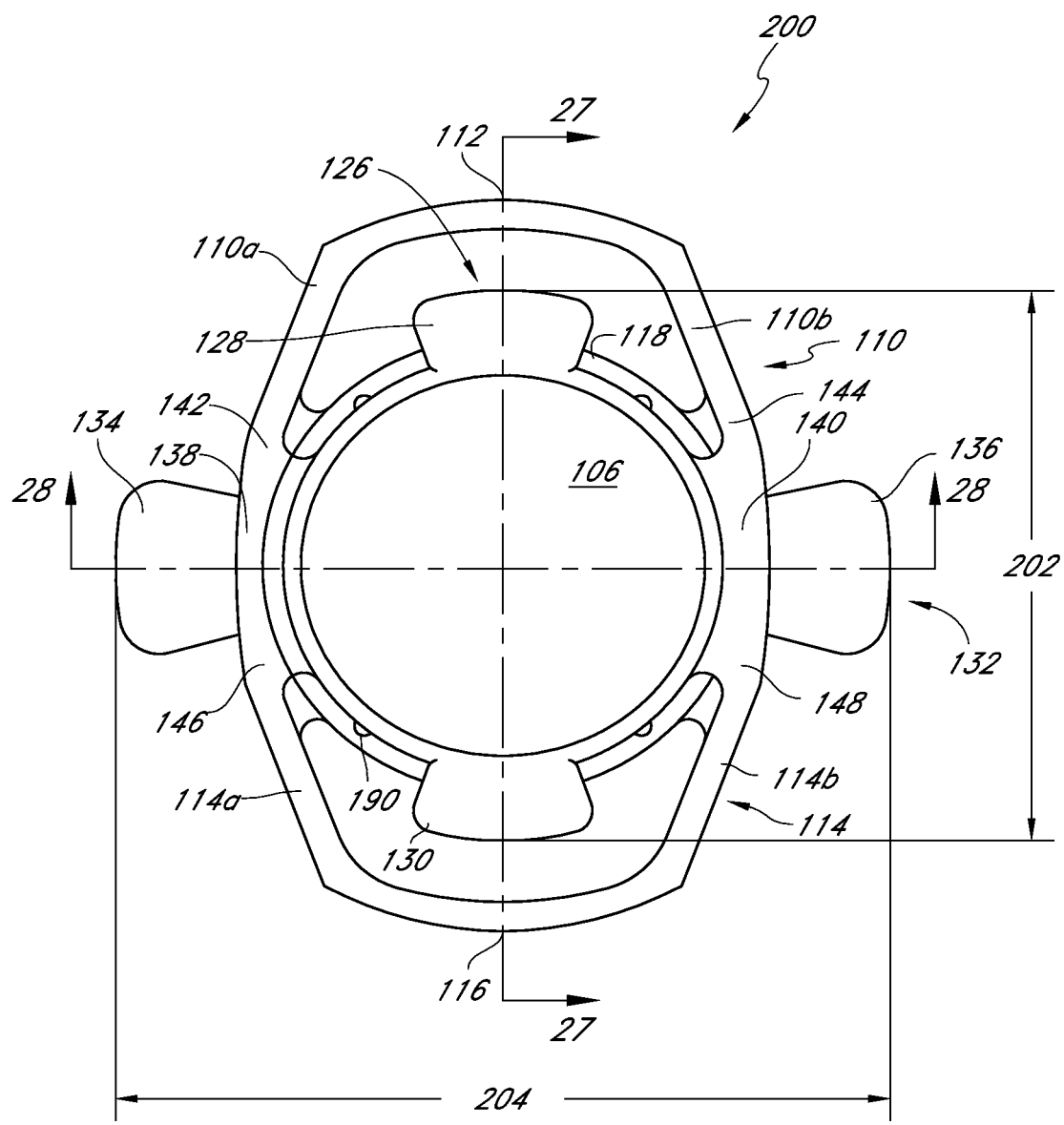
FIG. 26 is a front view of another embodiment of the lens system.
Figure 27:
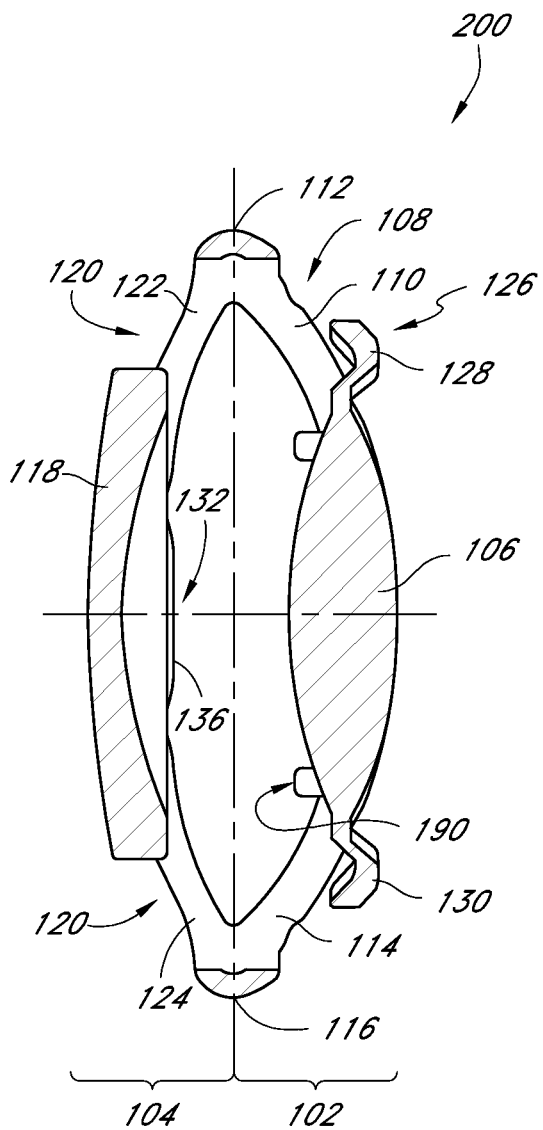
FIG. 27 is a side sectional view of the lens system of FIG. 26.
Figure 28:
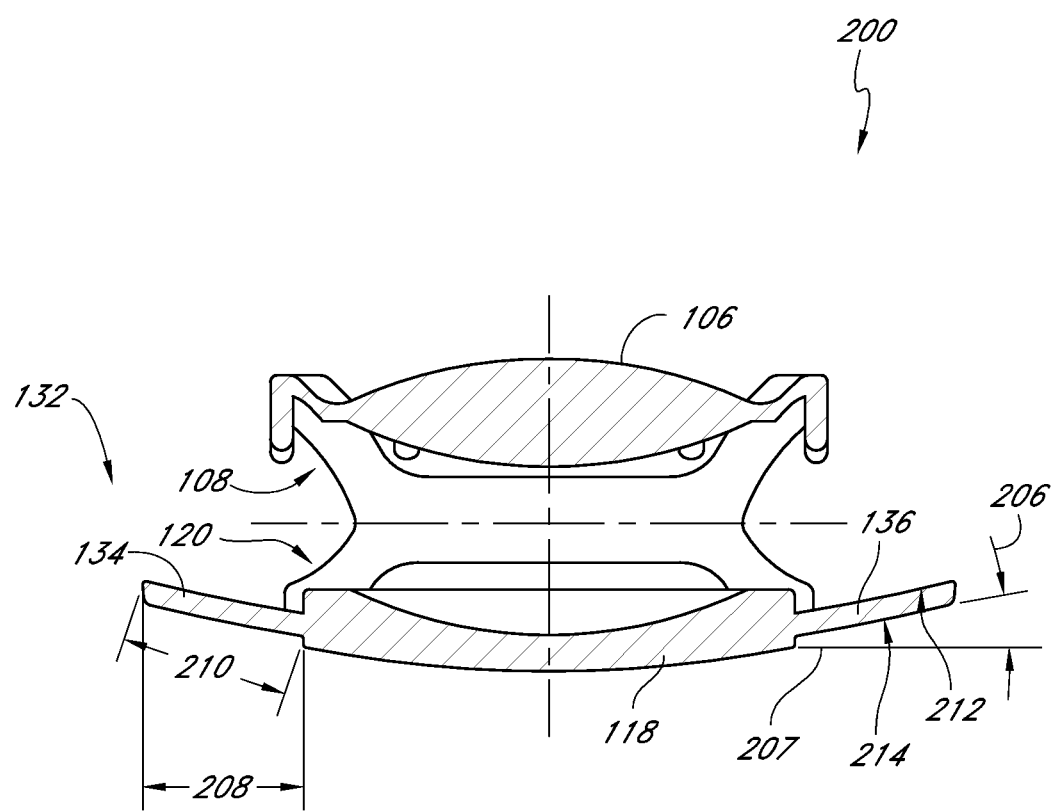
FIG. 28 is a top sectional view of the lens system of FIG. 26.

FIGS. 26-28 depict another embodiment 200 of the intraocular lens. It is contemplated that, except as noted below, this embodiment 200 may, in certain embodiments, be similar to any one or more of the embodiments disclosed in FIGS. 3-17 and FIGS. 21-25.

In the illustrated embodiment, the distance 202 between the free end 128b of the first retention member 128 and the free end 130b of the second retention member 130 preferably is between about 6 mm and about 8 mm. In one embodiment, the distance 202 preferably is between about 6.9 mm and about 7.3 mm.

In the illustrated embodiment, the distance 204 between the free end 134b of the first distending member 134 and the free end 136b of the second distending member 136 preferably is between about 8 mm and about 14 mm. In one embodiment, the distance 204 preferably is between about 9 mm and about 11 mm. In one embodiment, the distance 204 preferably is between about 9.7 mm and about 9.9 mm.

As shown in FIG. 28, the distending members 134, 136 preferably extend from the posterior viewing element 118 at an angle 206 measured with respect to a line 207 which is generally parallel to the lateral axis of the lens 200, as the lens 200 is viewed from above (i.e., along the transverse axis). In one embodiment, the angle 206 preferably is between about 10 degrees and about 25 degrees. The distending members 134, 136 extend from the posterior viewing element 118 by a distance 208 measured along the line 207, generally parallel to the lateral axis. The distance 208 preferably is between about 1 mm and about 4 mm. The length 210 of each of the distending members 134, 136 preferably is between about 1 mm and about 5 mm. In the illustrated embodiment, the distending members 134, 136 are slightly curved and have an anterior radius of curvature 212 of about 19.75 mm and a posterior radius of curvature 214 of about 20 mm.

Figure 29:
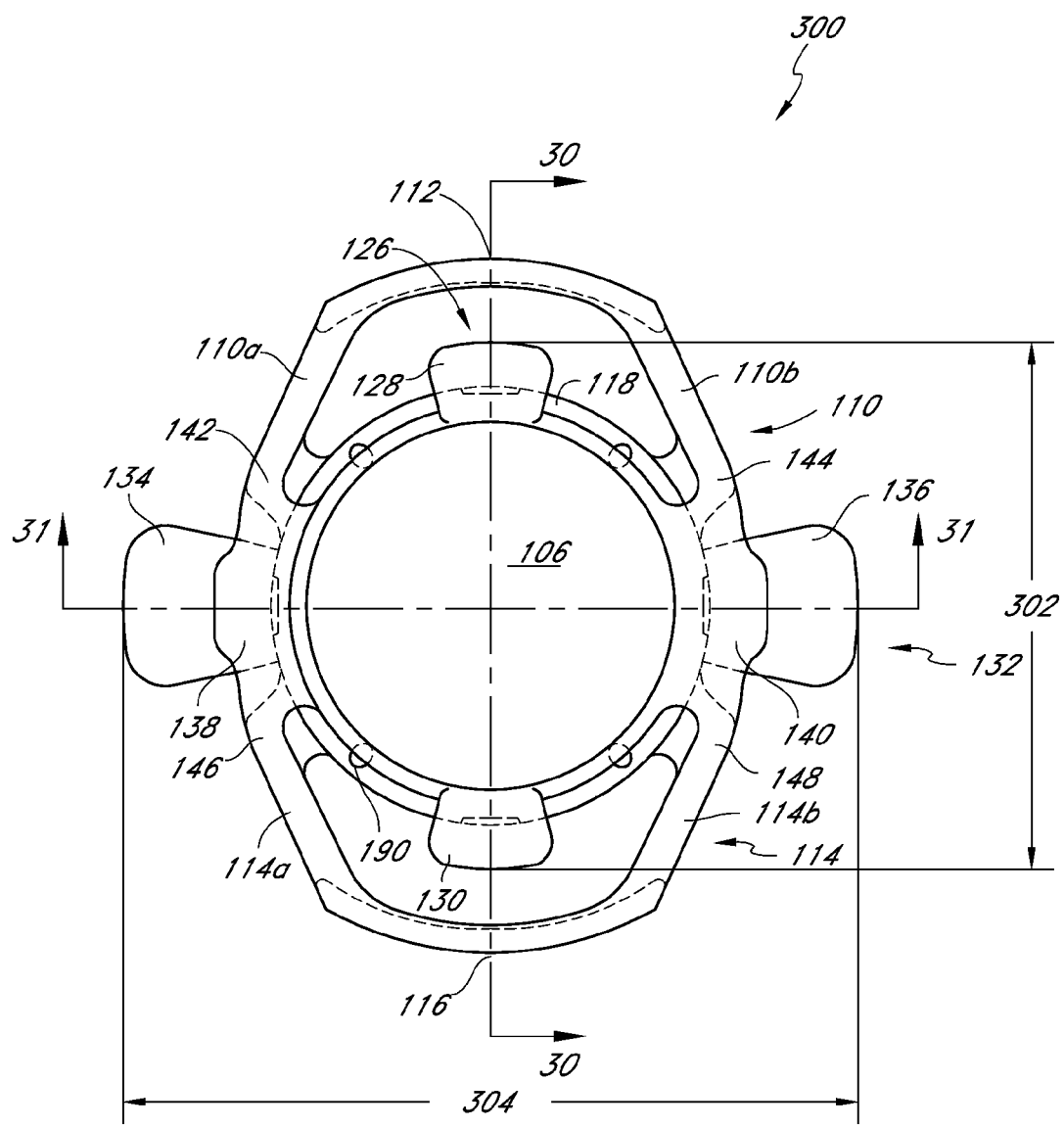
FIG. 29 is a front view of another embodiment of the lens system.
Figure 30:
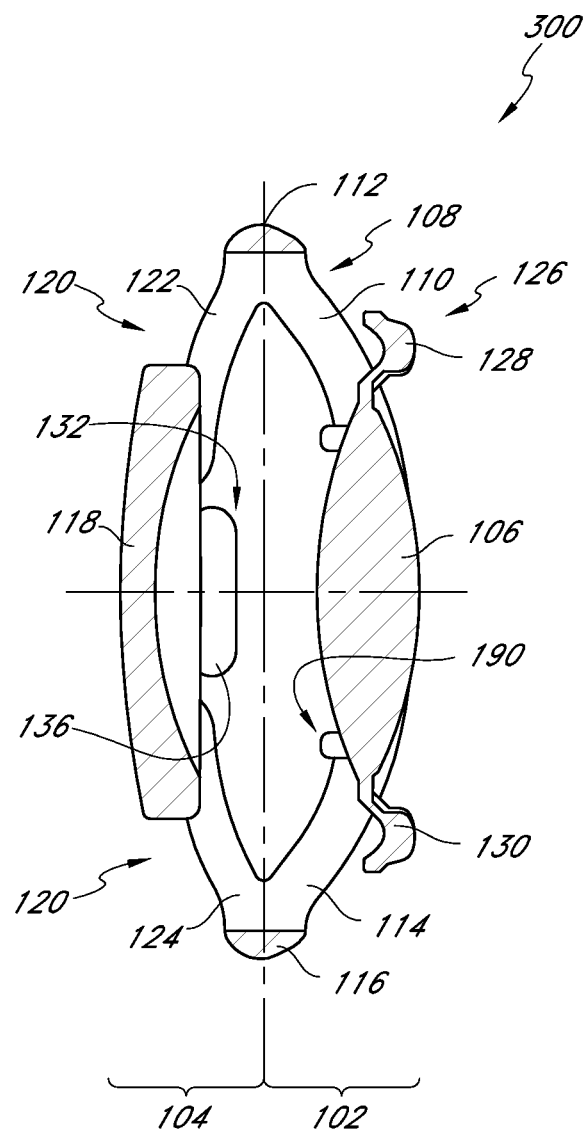
FIG. 30 is a side sectional view of the lens system of FIG. 29.
Figure 31:
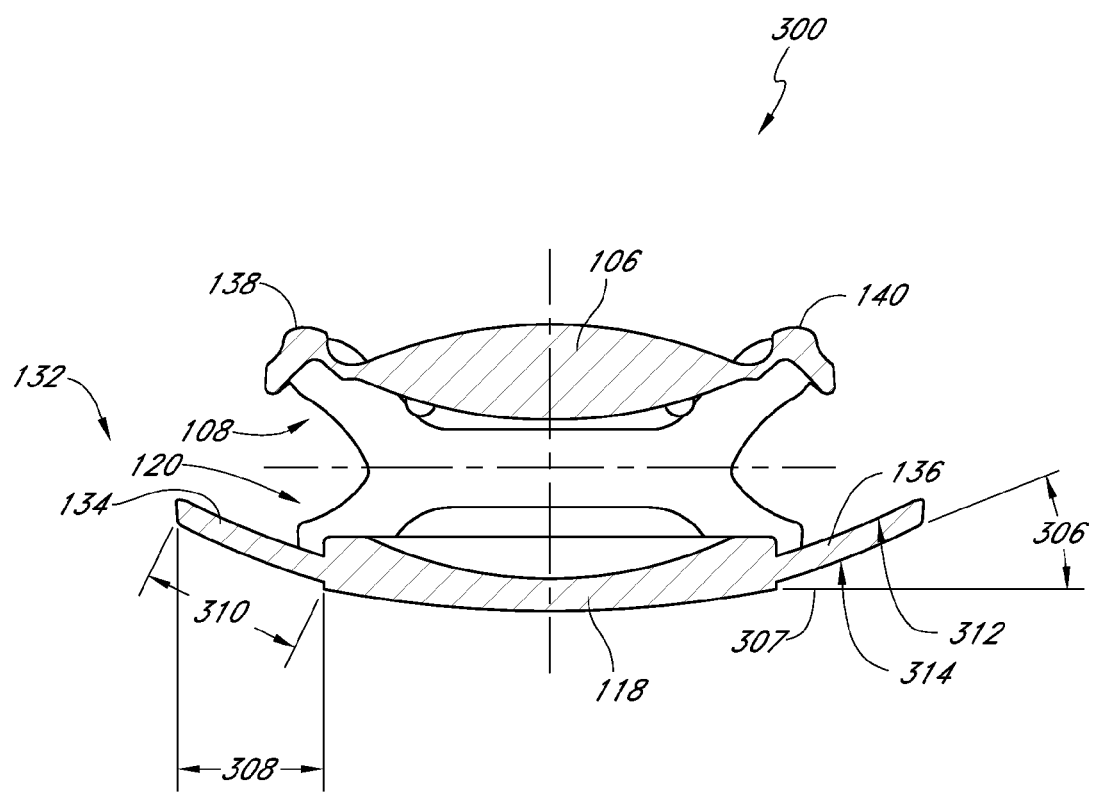
FIG. 31 is a top sectional view of the lens system of FIG. 29.

FIGS. 29-31 depict another embodiment 300 of the intraocular lens. It is contemplated that, except as noted below, this embodiment 300 may, in certain embodiments, be similar to any one or more of the embodiments disclosed in FIGS. 3-17, FIGS. 21-25, and FIGS. 26-28.

In the illustrated embodiment, the distance 302 between the free end 128b of the first retention member 128 and the free end 130b of the second retention member 130 preferably is between about 6 mm and about 8 mm. In one embodiment, the distance 302 preferably is between about 6.9 mm and about 7.3 mm.

In the illustrated embodiment, the distance 304 between the free end 134b of the first distending member 134 and the free end 136b of the second distending member 136 preferably is between about 8 mm and about 14 mm. In one embodiment, the distance 304 preferably is between about 9 mm and about 11 mm. In one embodiment, the distance 304 preferably is between about 9.7 mm and about 9.9 mm.

As shown in FIG. 31, the distending members 134, 136 preferably extend from the posterior viewing element 118 at an angle 306 measured with respect to a line 307 which is generally parallel to the lateral axis of the lens 300, as the lens 300 is viewed from above (i.e., along the transverse axis). In one embodiment, the angle 306 preferably is between about 20 degrees and about 40 degrees. The distending members 134, 136 extend from the posterior viewing element 118 by a distance 308 measured along the line 307, generally parallel to the lateral axis. The distance 308 preferably is between about 1 mm and about 4 mm. The length 310 of each of the distending members 134, 136 preferably is between about 1 mm and about 5 mm. In the illustrated embodiment, the distending members 134, 136 are slightly curved and have an anterior radius of curvature 312 of about 10.7 mm and a posterior radius of curvature 314 of about 11 mm.

FIGS. 32-37 depict another embodiment 400 of the intraocular lens. It is contemplated that, except as noted below, this embodiment 400 may, in certain embodiments, be similar to any one or more of the embodiments disclosed in FIGS. 3-17, FIGS. 21-25, FIGS. 26-28, and FIGS. 29-31.

In the illustrated embodiment, the distance 402 between the free end 128b of the first retention member 128 and the free end 130b of the second retention member 130 preferably is between about 6 mm and about 8 mm. In one embodiment, the distance 402 preferably is between about 6.9 mm and about 7.3 mm.

Figure 32:
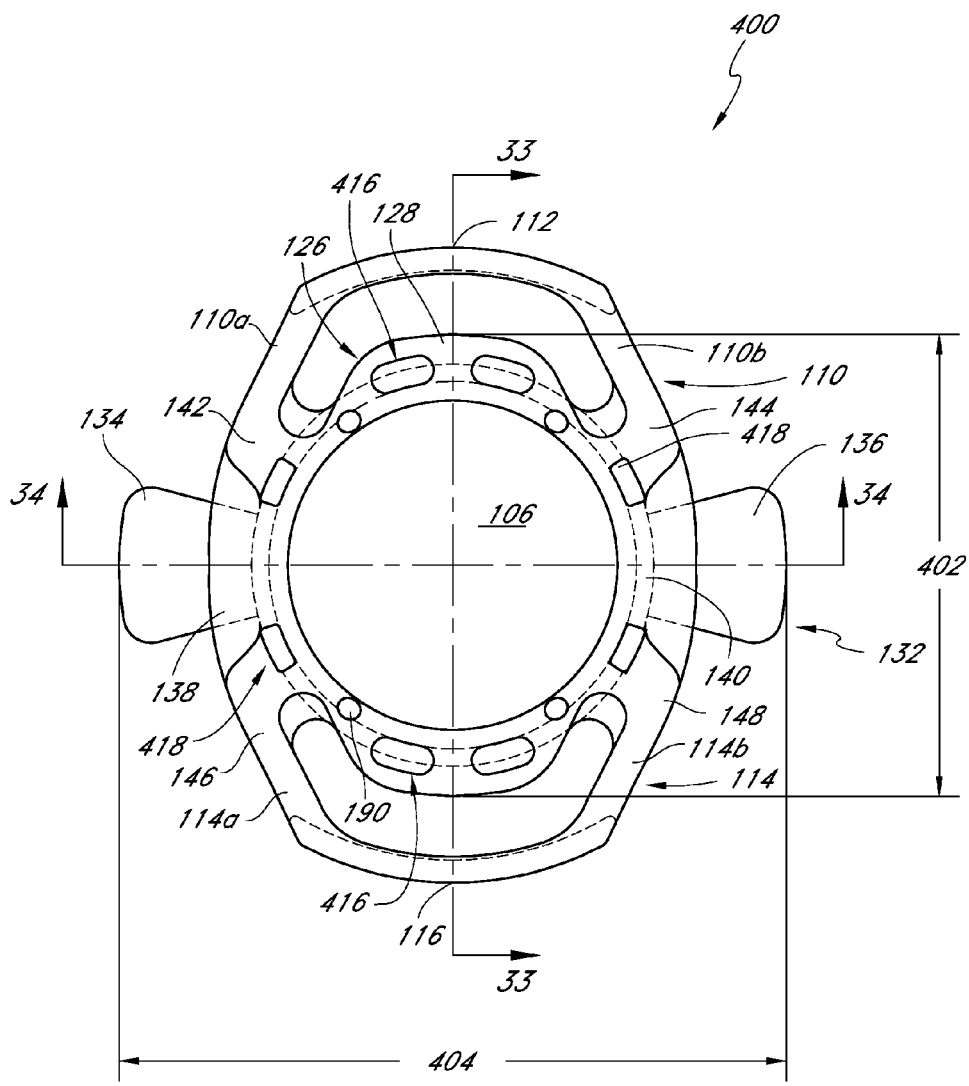
FIG. 32 is a front view of another embodiment of the lens system.
Figure 33:
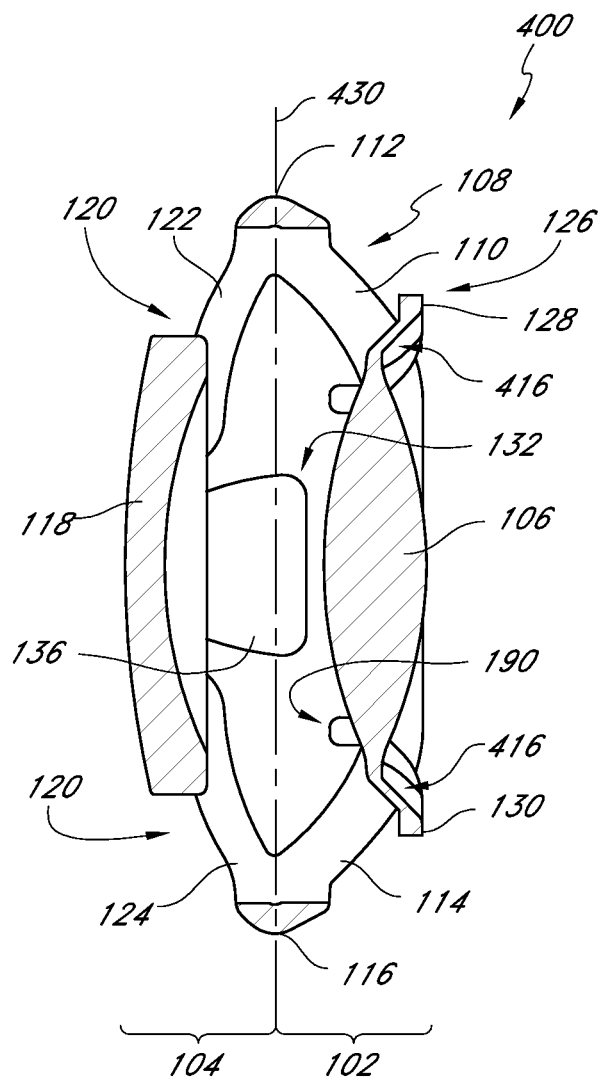
FIG. 33 is a side sectional view of the lens system of FIG. 32.
Figure 35:
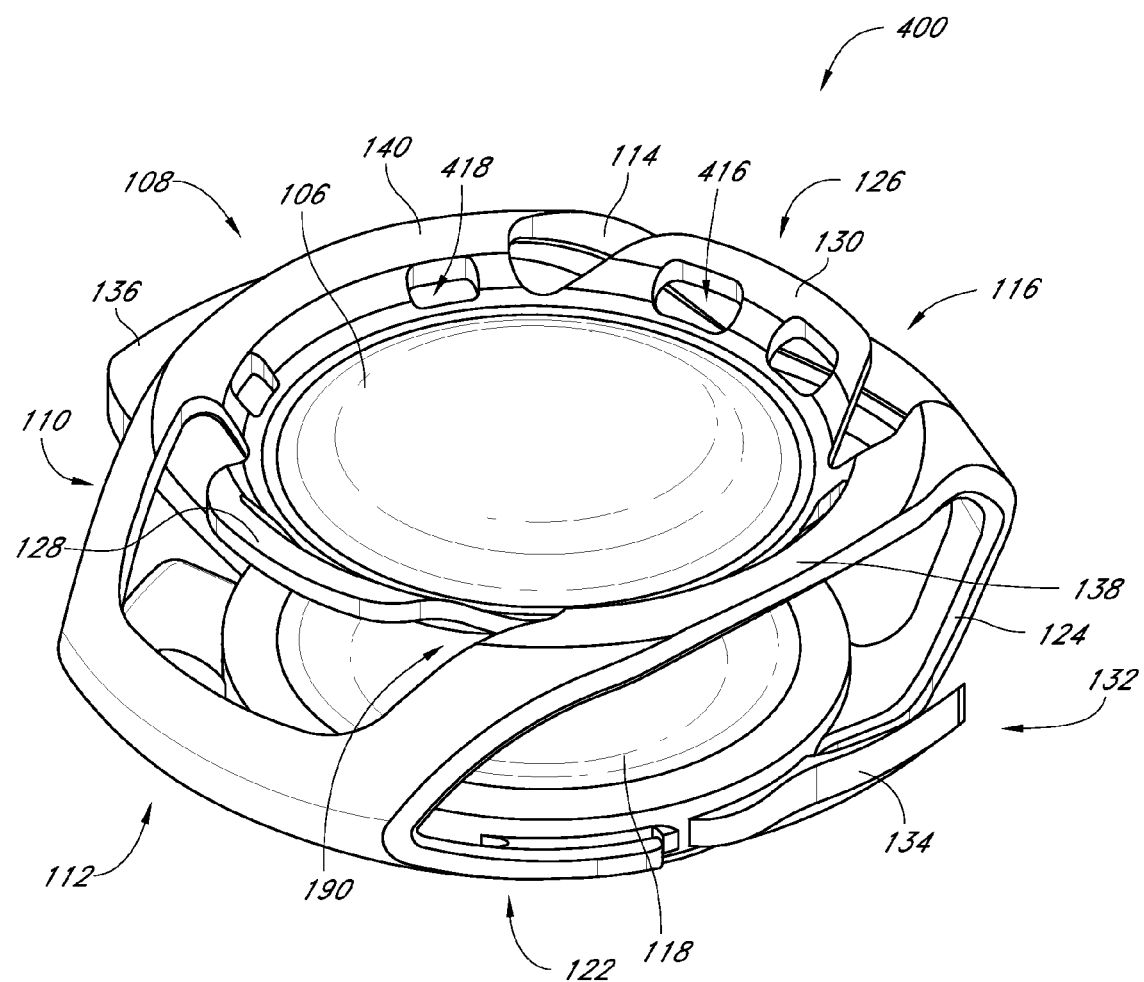
FIG. 35 is a perspective view of the lens system of FIG. 32.

As best shown in FIGS. 32 and 35, the retention members 128, 130 are preferably provided with openings 416. Likewise, the transition members 138, 140 are preferably provided with openings 418. These openings 416, 418 preferably permit fluid to flow between the interior of the capsular bag 58 and the portions of the eye anterior of the bag 58 as discussed further below.

In the illustrated embodiment, the distance 404 between the free end 134b of the first distending member 134 and the free end 136b of the second distending member 136 preferably is between about 8 mm and about 14 mm. In one embodiment, the distance 404 preferably is between about 9 mm and about 11 mm. In one embodiment, the distance 404 preferably is between about 9.7 mm and about 9.9 mm.

Figure 34:
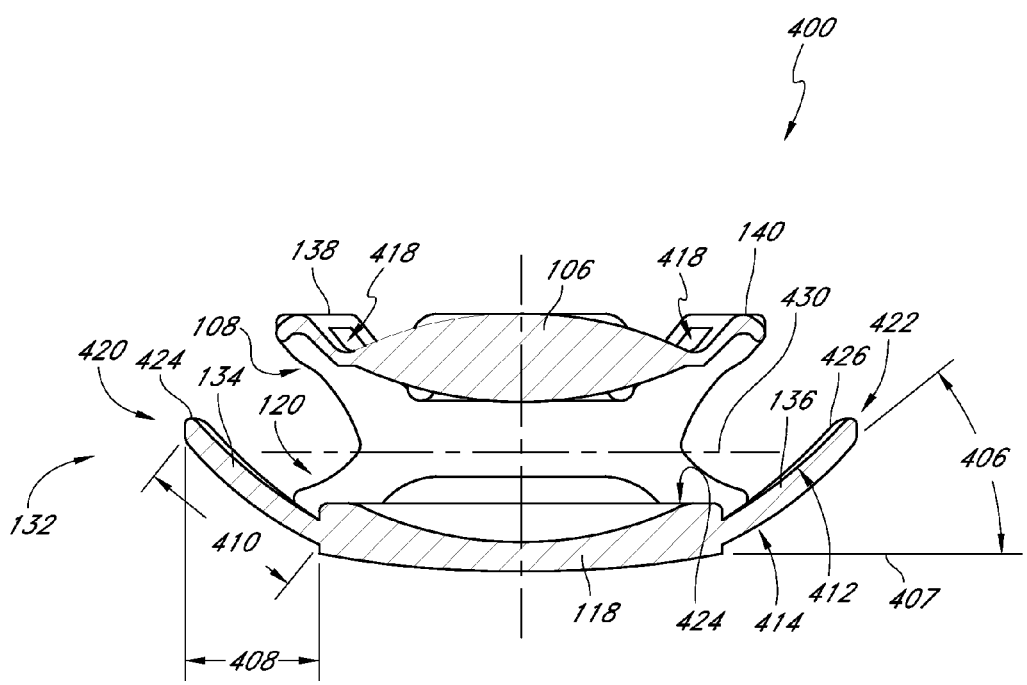
FIG. 34 is a top sectional view of the lens system of FIG. 32.

As shown in FIG. 34, the distending members 134, 136 preferably extend from the posterior viewing element 118 at an angle 406 measured with respect to a line 407 which is generally parallel to the lateral axis of the lens 400, as the lens 400 is viewed from above (i.e., along the transverse axis). In one embodiment, the angle 406 preferably is between about 10 degrees and about 55 degrees. In one embodiment, the angle 406 preferably is between about 20 degrees and about 40 degrees. In one embodiment, the angle 406 preferably is between about 25 degrees and about 35 degrees. The distending members 134, 136 extend from the posterior viewing element 118 by a distance 408 measured along the line 407 generally parallel to the lateral axis. The distance 408 preferably is between about 1 mm and about 4 mm. The length 410 of each of the distending members 134, 136 preferably is between about 1 mm and about 5 mm. In the illustrated embodiment, the distending members 134, 136 are slightly curved and preferably have an anterior radius of curvature 412 of about 6.2 mm and a posterior radius of curvature 414 of about 6.5 mm.

In one embodiment, at least one of the first and second distending members 134, 136 connected to the posterior portion 104 of the lens system 400 extends to a location 420 significantly anterior of an anterior surface 424 of the posterior viewing element 118. Preferably, first and second distending members 134, 136 are connected to the posterior portion 104 extend to first and second anterior locations 420, 422, respectively. Each of the first and second anterior locations 420, 422 is significantly anterior of the anterior surface 424 of the posterior viewing element 118.

As discussed previously, anterior and posterior biasing elements 108, 120 can be connected at first and second apices 112, 116. In one embodiment, each of the first and second anterior locations 420, 422 is spaced from the first and second apices 112, 116. In some embodiments, one or more of the distending members 134, 136 extends substantially to or beyond a plane 430 that passes through the apices 112, 116 and is oriented perpendicular to the optical axis. Preferably, one, both or all of the first and second anterior locations 420, 422 resides substantially at or anterior of a plane 430 that passes through the apices 112, 116 and is oriented perpendicular to the optical axis. In one embodiment, the first anterior location 420 comprises an anteriormost portion 424 of the first distending member 134, and the second anterior location 422 comprises an anteriormost portion 426 of the second distending member 136.

Figure 36:
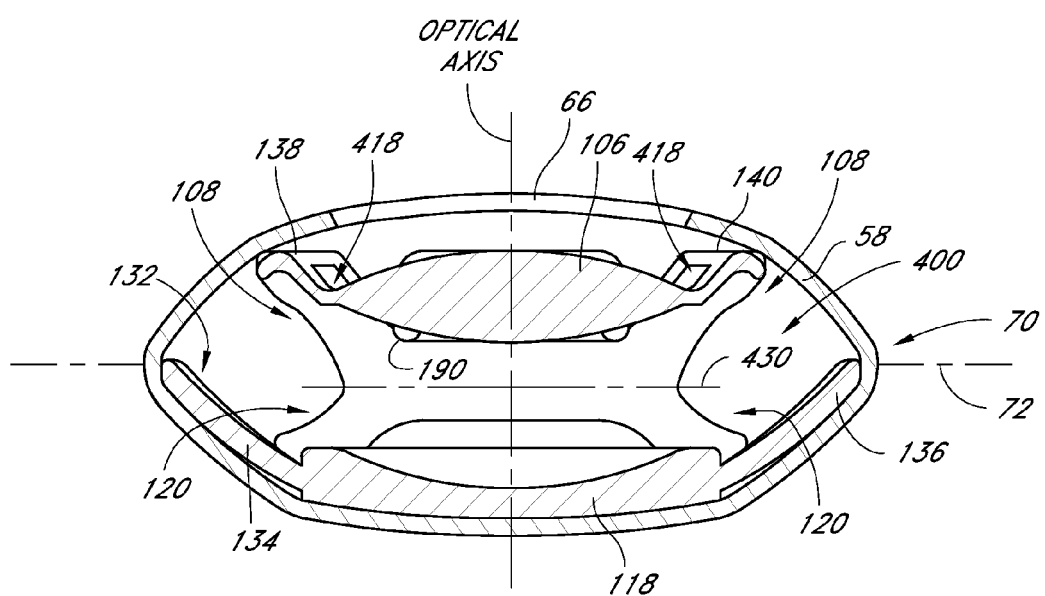
FIG. 36 is a top sectional view of the lens system of FIG. 32, implanted in a capsular bag.

FIG. 36 depicts the function of the distending portion 132 in greater detail. It is contemplated that, except as noted below, the function of the distending portion 132, in the illustrated embodiment 400, may be similar to the function of the embodiment described with reference to FIGS. 18-19.

The lens system 400 is shown situated in the capsular bag 58 in the customary manner with the anterior viewing element 106 and posterior viewing element 118 arranged along the optical axis. The capsular bag 58 is shown with a generally circular anterior opening 66 which may often be cut into the capsular bag during installation of the lens system 400. The first and second distending members 134, 136 of the distending portion 132 distend the capsular bag 58 so that intimate contact is created between the capsular bag 58 and the posterior face of the posterior viewing element and/or the posterior biasing element 120. In addition, intimate contact is facilitated between the capsular bag 58 and the anterior face of the anterior viewing element 106 and/or anterior biasing element 108. The distending members 134, 136 thus remove slack from the capsular bag 58 and ensure optimum force coupling between the bag 58 and the lens system 400 as the bag 58 is alternately stretched and released by the action of the ciliary muscle.

Figure 37:
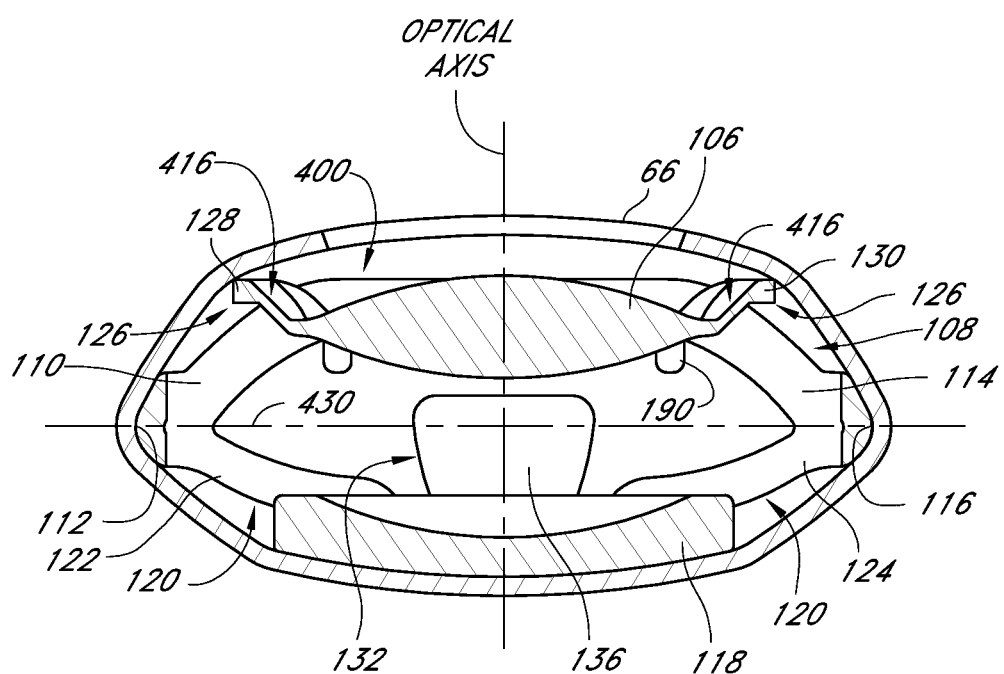
FIG. 37 is a side sectional view of the lens system of FIG. 32, implanted in a capsular bag.

The distending members 134, 136 preferably position or locate the lens system 400 in a desired orientation within the capsular bag. In one embodiment, the posterior viewing element 118 preferably is positioned in a posterior portion of the capsular bag 58. Typically, the capsular bag 58 has an apex 70 formed along an equator 72 of the capsular bag 58. The distending members 134, 136 preferably extend into the apex 70 to position the lens system 400. For example, the distending members 134, 136 preferably center the lens system 400 within the capsular bag 58 along the lateral axis. Additionally, in one embodiment, the distending members 134, 136 extend into the apex 70 of the capsular bag 58 and position the posterior viewing element 118 in a posterior portion of the capsular bag 58. In some embodiments, positioning the posterior viewing element 118 further posterior in the capsular bag 58 provides for a greater range of motion in response to the natural accommodation processes of the eye. With reference to FIGS. 27-36, any one or combination of the lengths 208, 308, 408, 210, 310, 410, angles 206, 306, 406, and curvatures 212, 312, 412, 214, 314, 414 of the distending members 134, 136 can be adjusted to control how far back the posterior viewing element 118 is positioned in the capsular bag 58. In some embodiments, the capsular bag 58 may be spaced from the posterior viewing element 118 a certain distance for an initial period of time following implantation of the system. In some embodiments, over time, the capsular bag 58 conforms to the shape of the posterior viewing element 118 as shown in FIGS. 36 and 37. The distending members 134, 136 preferably extend into the apex 70 formed along the equator 72 of the capsular bag 58 to maintain the lens system in a relatively stable position. In some embodiments, the distending members 134, 136 anchor the lens system relative the equator 72 of the capsular bag 58, to hold the posterior viewing element 118 in a desired configuration within a posterior portion of the capsular bag 58.

FIG. 37 shows the function of the retention portion 126 in greater detail. It is contemplated that, except as noted below, the function of the retention portion 126, in the illustrated embodiment 400, may be similar to the function of the embodiment described with reference to FIGS. 18-19.

As best seen in FIGS. 36 and 37, the anterior portion 102 of the lens system 400 forms a number of regions of contact with the capsular bag 58, around the perimeter of the anterior viewing element 106. In the illustrated embodiment, at least some of these regions of contact are located on the anterior-most portions of the anterior biasing element 108, specifically at the transition members 138, 140, and at the retention members 128, 130. As described above with respect to lens system 100, the transition members and the retention members define spaces therebetween at the edges of the anterior viewing element 106 to permit fluid to flow between the interior of the capsular bag 58 and the portions of the eye anterior of the bag 58. In other words, the anterior portion of the lens system 400 includes at least one location which is spaced from and out of contact with the capsular bag 58 to provide a fluid flow channel extending from the region between the viewing elements 106, 118 to the exterior of the bag 58.

Additionally, in the illustrated embodiment, openings 416, 418 are provided in the retention members 128, 130, and/or in the transition members 138, 140 to permit fluid to flow between the interior of the capsular bag 58 and the portions of the eye anterior of the bag 58. The sizes, configurations, and positions of the openings 416, 418 preferably are selected to allow adequate flow between the interior of the capsular bag 58 and the portions of the eye anterior of the bag 58. As noted above, if the anterior portion 102 of the lens system 400 seals the anterior opening 66 of the bag 58, the resulting prevention of fluid flow can cause the aqueous humor in the capsular bag to stagnate, leading to a clinically adverse event, and can inhibit the movement of the lens system 400 between the accommodated and unaccommodated states.

Although the function of the distending portion 132 and retention portion 126 are described with reference to lens system 400, other embodiments, such as for example, lens system 200 and lens system 300, preferably can function in a similar manner.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. An accommodating intraocular lens (IOL) for implantation in an eye, the lens having an optical axis, comprising:
    an anterior viewing element having a circumference and comprising an anterior optic;
    a posterior viewing element having a circumference and comprising a posterior optic;
    a biasing system comprising first and second anterior translation arms connected to said anterior viewing element, and first and second posterior translation arms connected to said posterior viewing element, said anterior and posterior translation arms meeting at first and second equatorial apices of said intraocular lens, said biasing system connecting said anterior viewing element and said posterior viewing element for relative movement of said anterior optic relative to said posterior optic along the optical axis between an accommodated state and an unaccommodated state in response to force generated within the eye, said biasing system biasing said anterior viewing element and said posterior viewing element toward the accommodated state in absence of external forces;
    a first arcuate transition member having an end coupled to said anterior viewing element and having an opposite end coupled to the first anterior translation arm of said biasing system, said first transition member disposed around at least a portion of the circumference of said anterior viewing element and extending anteriorly and radially outward of said anterior viewing element, said first transition member comprising at least one opening there through, said at least one opening configured to provide fluid flow passages between an interior of a capsular bag of an eye into which the lens has been inserted and portions of the eye anterior of the capsular bag,
    a second arcuate transition member having an end coupled to the circumference of said anterior viewing element and having an opposite end coupled to the second anterior translation arm of said biasing system, said second transition member disposed around at least a portion of the circumference of said anterior viewing element and extending anteriorly and radially outward of said anterior viewing element, said second transition member comprising at least one opening there through, said at least one opening configured to provide fluid flow passages between an interior of a capsular bag of an eye into which the lens has been inserted and portions of the eye anterior of the capsular bag; and
    first and second distending members coupled to diametrically opposed portions of the circumference of the posterior viewing element, each of said first and second distending members extending to locations significantly anterior of an anterior side of the posterior viewing element.

2. The lens of claim 1, wherein said at least one opening is located radially inward of an anteriormost portion of said first or second transition member relative to the optical axis of the lens.

3. The lens of claim 1, wherein said first and second transition members are evenly spaced around said anterior viewing element.

4. The lens of claim 3, wherein said first and second transition members are diametrically opposed.

5. The lens of claim 1, wherein each of the first and second transition members includes an inclined member having a lower portion disposed about and coupled to the anterior viewing element and an upper portion disposed radially outward from the lower portion.

6. The lens of claim 5, wherein the inclined member has an inclined surface comprising the openings.

7. The lens of claim 5, wherein each of the anterior translation arms have a first end coupled with the upper portion of the inclined member and a second end coupled with the first or second equatorial apices.

8. The lens of claim 1, wherein the anterior viewing element or the posterior viewing element has an aspheric surface.

* * * * *